УС005912125A

United States Patent [19]
Peck et al.

[11] Patent Number: 5,912,125
[45] Date of Patent: Jun. 15, 1999

[54] MATERIALS AND METHODS FOR DETECTION OF OXALOBACTER

[75] Inventors: Ammon B. Peck; Harmeet Sidhu, both of Gainesville, Fla.

[73] Assignee: University of Florida, Gainesville, Fla.

[21] Appl. No.: 08/717,587

[22] Filed: Sep. 27, 1996

Related U.S. Application Data

[63] Continuation-in-part of application No. 08/493,197, Jun. 20, 1995, which is a continuation-in-part of application No. 08/262,424, Jun. 20, 1994, Pat. No. 5,604,111.

[51] Int. Cl.[6] .............................. C12Q 1/68; C12P 19/34; C07H 19/00
[52] U.S. Cl. ........................... 435/6; 435/91.1; 435/91.2; 536/22.1; 536/24.1; 536/24.33; 536/23.7
[58] Field of Search ............................. 435/6, 91.1, 91.2; 536/22.1, 24.1, 24.33, 23.7; 935/76, 77, 78

[56] References Cited

U.S. PATENT DOCUMENTS 5,043,272 8/1991 Hartley ....................................... 435/91

OTHER PUBLICATIONS

Lung et al. "Cloning and Expression of the Oxalyl–CoA Decarboxylase Gene From the Bacterium, Oxalobacter formigenes: Prospects for Gene Therapy to Control Ca–Oxalate Kidney Stone Formation" Am. J. Kidney Dis., vol. 17, pp. 381–385, 1991.

Lung et al. "Molecular Cloning, DNA Sequence and Gene Expression of the Oxalyl–Coenzyme A Decarboxylase Gene, oxc, from the Bacterium Oxalobacter formigenes" Journal of Bacteriology, vol. 176, No. 8, pp. 2468–2472, Apr. 1994.

Stratagene Catalog p.39, 1988.
New England Biolabs Catalog, Beverly, MA, USA, p. 61, 1986.

Hodgkinson, A. (1970) "Determination of Oxalic Acid in Biological Material" Clinical Chemistry 16(7):547–557.
Curhan, Gary C. M.D. et al. (1993) "A Prospective Study of Dietary Calcium and Other Nutrients and the Risk of Symptomatic Kidney Stones" N.E.J. Med. 328(12):833–838.
Costello, J. M. Hatch, E. Bourke (1976) "An enzymatic method for the spectrophotometric determination of oxalic acid" J. Lab. Clin. Med. 87(5):903–908.
Baetz, A.L., M.J. Allison (1989) "Purification and Characterization of Oxalyl–Coenzyme A Decarboxylase from Oxalobacter formigenes" Journal ob Bacteriology 171(5):2605–2608.
Baetz, A.L., M.J. Allison (1990) "Purification and Characterization of Formyl–Coenzyme A Transferease form Oxalobacter formigenes" Journal of Bacteriology 172(7):3537–3540.

(List continued on next page.)

*Primary Examiner*—Ardin H. Marschel
*Assistant Examiner*—Jezia Riley
*Attorney, Agent, or Firm*—Saliwanchik, Lloyd & Saliwanchik

[57] ABSTRACT

The subject invention concerns the novel use of formyl-CoA transferase enzyme together with oxalyl-CoA decarboxylase enzyme for the detection and measurement of oxalate in biological samples. The use of the enzyme system according to the subject invention results in the conversion of oxalate into carbon dioxide and formate. Because the production of formate is directly correlated to the concentration of oxalate present in a sample, the determination of the resulting formate concentration provides an accurate, sensitive and rapid means for detecting even low levels of oxalate. The subject invention further concerns the cloning, sequencing and expression of the genes that encode the formyl-CoA transferase enzyme and the oxalyl-CoA decarboxylase enzyme of *Oxalobacter formigenes*. The subject invention also concerns methods for detecting the presence of *Oxalobacter formigenes* organisms in a sample, and the polynucleotide probes and primers used in the detection method.

10 Claims, 12 Drawing Sheets

OTHER PUBLICATIONS

Yriberri, J., S. Posen (1980) "A Semi–Automatic Enzymic Method for Estimating Urinary Oxalate" Clin. Chem. 26(7):881–884.

Allen, L.C. et al. (1989) "An Enzymatic Method for Oxalate Automated with the Cobas Fara Centrifugal Analyzer" Clin. Chem. 35(10):2098–2100.

Li, M.G., M.M. Madappally (1989) "Rapid Enzymatic Determination of Urinary Oxalate" Clin. Chem 35(12):2330–2333.

Santamaria, J.R., R. Coll, E. Fuentespina (1993) "Comparative Study of Two Commercial Enzymatic Kits for Determining Oxalate Concentrations in Urine" Clin. Biochem. 26:93–96.

"Urologicals" (Descriptive Flier) with attached table of "StoneRisk Profile" and p. 732 IV. Urologic: Diseases of the Genitourinary Tract.

Infantes, J.A. et al.(1991) "Kinetic–enzymatic determination of oxalate in urine by flow injection analysis with double stopped flow" Analytica Chimica Acta. 242:179–183.

Costello, J.F., Smith, M. (1992) "Determination of Evolved $^{14}CO_2$ in Decarboxylase Reactions with Application to Measurement of [$^{14}C$]Oxalic Acid" Analytical Biochemistry 202:337–339.

Binette, Y., J.–G. Durocher (1985) "Le Dosage des Oxalates Urinaires: Comparaison de Trois Methodes" Ann. Biochem. Clin. Que. 24(3):93–96.

Hatch, M., R.W. Freel (1995) "Oxalate Transport Across Intestinal and Renal Epithelia" Calcium Oxalate in Biological Systems, pp. 217–238.

Dawson, K.A. et al. (1980) Isolation and Some Characteristics of Anaerobic Oxalate–Degrading Bacteria from the Rumen Applied and Environmental Microbiology 40(4):833–839.

Anderson, J.T. et al. (1993) "Insulin–Dependent Diabetes in the NOD Mouse Model II. β Cell Destruction in Autoimmune Diabetes is a $T_{H2}$ and not a $T_{H1}$ Mediated Event" Autoimmunity 15:113–122.

Stacy–Phipps, S. et al. (1995) "Multiplex PCR Assay and Simple Preparation Method for Stool Specimens Detect Enterotoxigenic Escheria Coli DNA during Course of Infection" Journal of Clinical Microbiology33(5):1054–1059.

Allison, M.J. et al. (1985) "Oxalobacter formigenes gen. nov., sp. nov.: oxalate degrading bacteria that inhabit the gastrointestinal tract" Arch. Microbiol. 141:1–7.

Jensen, N.S. et al. (1994) "Studies on the diversity among anaerobic oxalate–degrading bacteria now in the species Oxalobacter formigenes" Abst. Ann. Mtg. Amer. Soc. Microbial., pp. 1–29.

```
                        Hind III site
                        -161↓
-109    ....AAGCTTCATTTGAGATGTTATGCGAAGTGTTAGCAACCAAGTTAGTA
  -1    CCCTTCAGCCCCTTTGGGCGAAGTTTTTCTTCTTCGGGGAAACAGCACAGAGAATAAAAACCAAAAGTTGTACCAACGACAAGGAAATGAGAAATT
        M  T  K  P  L  D  G  I  N  V  L  D  F  T  H  V  Q  A  G  P  A  C  T  Q  M  M  G  F  L  G  A  N  V  I  K  I
 108    ATGACTAAACCATTAGATGGAATTAATGTGCTTGACTTTACCCACGTCCAGGCAGGTCCTGCCTGTACACAGATGATGGGTTTCTTGGGCGCAAACGTCATCAAGATT
                                     >----5'-primer---->
                                                                                              TRYPSIN DIGEST
        E  R  R  G  S  G  D  M  T  R  G  W  L  Q  D  D  K  P  N  V  D  S  L  Y  F  T  M  F  N  C  N  K  R  S  I  E  L
 216    GAAAGACGTGGTTCCGGAGATATGACTCGTGGATGGCTGCAGGACGACAAACCAAATGTTGATTCCCTGTATTTCACGATGTTCAACTGTAACAAACGTTCAATGAACTG
                                                                                                        <---3'-primer--
        D  M  K  T  P  E  G  K  E  L  L  E  Q  M  I  K  K  A  D  V  M  V  E  N  F  G  P  G  A  L  D  R  M  G  F  T
 324    GACATGAAAACCCCGGAAGGCAAAGAGCTTCTGGAACAGATGATCAAGAAGGCCGACGTCATGGTCGAAAACTTCGGACCAGGCGCACTGGACCGTATGGGCTTTACT
        <-------<
        W  E  Y  I  Q  E  L  N  P  R  V  I  L  A  S  V  K  G  Y  A  E  G  H  A  N  E  H  L  K  V  Y  E  N  V  A  Q
 432    TGGGAATACATTCAGGAACTGAATCCACGCGTCATTCTGGCTTCCGTTAAAGGCTATGCAGAAGGCCACGCCAACGAACACCTGAAAGTTTATGAAAACGTTGCACAG
              <----3'-primer----<
        C  S  G  A  A  A  T  T  G  F  W  D  G  P  P  T  V  S  G  A  A  L  G  D  S  N  S  G  M  H  L  M  I  G  I
 540    TGTTCCGGGGCTGCTGCAGTCGACTACCACCGGTTTCTGGGATGGTCCTCCAACCGTTCCTCAAACTCCGGTATGCACCTGATGATCGGTATT
        L  A  L  E  M  R  H  K  T  G  R  G  Q  K  V  A  V  A  M  Q  D  A  V  L  N  L  V  R  I  K  L  R  D  Q  Q
 648    CTGGCCGCTCTGGAAATGCGTCACAAAACCGGCCGTGGTCAGAAAGTTGCCGTCGCTATGCAGGACGCTGTTCTGAATCTGGTTCGTATCAAACTGCGTGACCAGCAA
```

FIG. 2A

```
                                                                                                           756
R  L  E  R  T  G  I  L  A  E  Y  P  Q  A  Q  P  N  F  A  F  D  R  D  G  N  P  L  S  F  D  N  I  T  S  V  P
CGTCTGGAAAGAACCGGCATTCTGGCTGAATACCCAGGCTCAGCCTAACTTTGCCTTCGACAGAGACGGTAACCCACTGTCCTTCGACAACATCACTTCCGTTCCA
                                                                                                           864
R  G  G  N  A  G  G  G  G  Q  P  G  W  M  L  K  C  K  G  W  E  T  D  A  D  S  Y  V  V  Y  F  T  I  A  A  N  M
CGTGGGGTAACGCAGGTGGCGGCGGCCAGGCTGGATGCTGAAATGTAAAGGTTGGGAAACCGATGCGGACTCCTACGTTACTTCACCATCGCTGCAAACATG
                                                                                                           972
W  P  Q  I  C  D  M  I  D  K  P  E  W  K  D  D  P  A  Y  N  T  F  E  G  R  V  D  K  L  M  D  I  F  S  F  I
TGGCCACAGATCTGCGACATGATCGACAAGCCAGAATGGAAAGACGACCCAGCTACAACACATTCGAAGGTCGTGTTGACAAGCTGATGGACATCTTCTCCTTCATC
                                                                                                           1080
E  T  K  F  A  D  K  D  K  F  E  V  T  E  W  A  A  Q  Y  G  I  P  C  G  P  V  M  S  M  K  E  L  A  H  D  P
GAAACCAAGTTCGCTGACAAGGACAAGTTCGAAGTTACCGAATGGGCTGCCCAGTACGGCCATTCCTTGCGGTCCGGTCATGTCCATGAAAGAACTGGCTCACGATCCT
                                                                                                           1188
S  L  Q  K  V  G  T  V  V  E  V  V  V  D  E  I  R  G  N  H  L  T  V  G  A  P  F  K  F  S  G  F  Q  P  E  I  T
TCCCTGCAGAAAGTTGGTACCGTCGTTGAAGTTGTCGACGAAATTCGTGGCAACCACCTGACCGTTGGCGCTCCGTTCAAATTCTCCGGATTCCAGCCGGAAATTACC
                                                                                                           1296
                                                                                                    1284
R  A  P  L  L  G  E  H  T  D  E  V  L  K  E  L  G  L  D  D  A  K  I  K  E  L  H  A  K  Q  V  V ter
CGTGCTCCGCTGTTGGGCGAACATACCGACGAAGTTCTGAAAGAACTGGGTCTTGACGATGCCAAGATCAAGGAACTGCATGCAAAACAGGTAGTTGATCCGTCAGA
                                                                                                           1404
CTTTCTGGGCAAAAACGGCACTCTCCGGAGTGCCGTTTTTGTCACACGAAACCTAATCAAACAAGCACGTGAATGATTCCACATCATTGCGGCCACATTCATCCTTC
1416
GGGTCATTACTG........
```

```
-180                        -172                      -139                      -124                                                  -100         -91        -81
ATTTGTTTAAATTGACCTGATCAATATTGCCGGATTGATCAATTGATCAATTGACTTATGTCAATGAATTGACTTATGTCAATGGTGCCAAATTGACCTAGGTCAACGG
                                -151                       -132                                                                                      -14          20
                                                                                                                                                M  S  N  D  D  N  V
-80  GATTTTAAAGGGTATGCGGCATACTCGGAATTGACGTTAAACAACGTTTATCAAACCAACCAAGAAGAAGGTATTACTCATGAGTAACGACGACAATGT
                                                                                                                                                                 120
      E  L  T  D  G  F  H  V  L  I  D  A  L  K  M  N  D  I  D  T  M  Y  G  V  V  G  I  P  I  T  N  L  A
 21  AGAGTTGACTGATGGCTTCATGTTTTGATCGATGCCCTGAAAATGAATGACATCGATACCATGTATGGTGTTGTCGGCATTCCTATCACGAACCTGGCT
                                                                                                                                                                 220
      R  M  W  Q  D  D  G  Q  R  F  Y  S  F  R  H  E  Q  H  A  G  Y  A  A  S  I  A  G  Y  I  E  G  K  P
121  CGTATGTGGCAAGATGACGGTCAGCGTTTTACAGCTTCCGTCACGAACAACGCCAGGTTATGCAGTTCTATCGCCGGTTACATCGAAGGAAAACCTG
                                                                                                                                                                 320
      G  V  C  L  T  V  S  A  P  G  F  L  N  G  V  T  S  L  A  H  A  T  T  N  C  F  P  M  I  L  L  S  G  S
221  GCGTTTGCTTGCTTGACCGTTCCGCCCCTGGCTTCCCTGAACGGGTGACTTCCCTGGCTCATGCAACCACCAACTGCTTCCCAATGATCCTGTTGAGCGGTTC
                                                                                                                                                                 420
      S  R  E  I  V  D  L  Q  Q  G  D  Y  E  E  M  D  Q  M  N  V  A  R  P  H  C  K  A  S  F  R  I  N
321  CAGTGAACGTGAAATCGTCGATTCGAAGACGGTGACGGGCGATTACGAAGAATGGATCAGATGTTGCACGTCCACACTGCAAAGCTTCTTTCCGTATCAAC
                                                                                                                                                                 520
      S  I  K  D  I  P  I  G  I  A  R  A  V  R  T  A  V  S  G  R  P  G  G  V  Y  V  D  L  P  A  K  L  F
421  AGCATCAAAGACATTCCAATCGGTATCGCTCGTGCAGTTCGCACCGCCGTGTATCCGGACGTCGTTGTTTACGTTGACTTGCCAGCAAAACTGTTCG
                                                                                                                                                                 620
      G  Q  T  I  S  V  E  E  A  N  K  L  L  F  K  P  I  D  P  A  P  A  Q  I  P  A  E  D  A  I  A  R  A  A
521  GTCAGACCATTTCTGTAGAAGAAGCTAACAAACTGCTCTTCAAACCAATCGATCCAGCTCCGGCACAGATTCTTGCTGAAGACGTATCGCTGCGCTGC
                                                                                                                                                                 720
      D  L  I  K  N  A  K  R  P  V  I  M  L  G  K  A  A  Y  A  Q  C  D  D  E  I  R  A  L  V  E  E  T
621  TGACCTGATCAAGAACGCCAAACGTCCAGTTATCATGTGGGTAAAGGCGCTGCATACGCGACACAATGCGACGACGAAATCCGGCACTGGTTGAAGAAACC
                                                                                                                                                                 820
      G  I  P  F  L  P  M  G  M  A  K  G  L  L  P  D  N  H  P  Q  S  A  A  A  T  R  A  F  A  L  A  Q  C
721  GGCATCCCATTCCTGCCAATGGGTATGGCTAAAGGCCTGCTGCCTGACAACCATCCACAATCCGCTGCTGACACCCGTGCTTTCGCACTGGCACAGTGTG
                                                                                                                                                                 920
      D  V  C  V  L  I  G  A  R  L  N  W  L  M  Q  H  G  K  G  K  T  W  G  D  E  L  K  K  Y  V  Q  I  D  I
821  ACGTTTGCGTGCTGATCGGGGCTCGTCTGAACTGGCTGATGCAGCACGGTAAAGGCAAAACCTGGGGCGACGAACTGAAGAAATACGTTCAGATCGACAT
```

FIG. 3B

```
       Q  A  N  E  M  D  S  N  Q  P  I  A  A  P  V  V  G  D  I  K  S  A  V  S  L  L  R  K  A  L  K  G  A
 921   CCAGGCTAACGAAATGGACAGCAACCAGCCTATCGCTGCACCAGTTGTTGGTGACATCAAGTCCGCCGTTTCCCTGCTCCGCAAAGCACTGAAAGGCGCT    1020
       P  K  A  D  A  E  W  T  G  A  L  K  A  K  V  D  G  N  K  A  K  L  A  G  K  M  T  A  E  T  P  S  G
1021   CCAAAAGCTGACGCTGAATGGAACCGGCGCTCTGAAAGCTAAAGTTGACGGCAACAAAGCCAAACTGGCTGGCAAGATGACTGCCGAAACCCATCCGGAA    1120
       M  M  N  Y  S  N  S  L  G  V  V  R  D  F  M  L  A  N  P  D  I  S  L  V  N  E  G  A  N  A  L  D  N  T
1121   TGATGAACTACTACTCCAATTCCCTGGGCGTTGTTCGTGACTTCATGCTGGCAAATCCGGATATATTCCCTGGTTAACGAAGGCGCTAATGCACTCGACAACAC    1220
       R  M  I  V  D  M  L  K  P  R  K  R  L  D  S  G  T  W  G  V  M  G  I  G  M  G  Y  C  V  A  A  A
1221   TCGTATGATTGTTGACATGCTGAAACCGCGCAAACCACGCCTCTTGACTCCGGTACCTGGGGTGTTATGGGTATTGGTATGGGCTACTGCGTTGCTGCAGCTGCT    1320
                                                                            [-------TPP Binding Motif-------    1420
       V  T  G  K  P  V  I  A  V  E  G  D  S  A  F  G  F  S  G  M  E  L  E  T  I  C  R  Y  N  L  P  V  T
1321   GTTACCGGCAAACCGGTTATCGCTGTTGAAGGCGATAGCGCATTCGGTTTCTCCGGTATGGAACTGGAAACCATCTGCCGTTACAACCTGCCAGTTACCG    1420
       V  I  I  M  N  N  G  G  I  Y  K  G  N  E  A  D  P  Q  P  G  V  I  S  C  T  R  L  T  R  G  R  Y  D  M
1421   ------]TTATCATCATGAACAATGGTGGTATCTATAAAGGTAACGAAGCAGATCCACAACCAGGCGTTATCTCCTGTACCCGTCTGACCCGTGGTCGTTACGACAT    1520
       M  M  E  A  F  G  G  K  G  Y  Y  V  A  N  T  P  A  E  L  K  A  A  L  E  E  A  V  A  S  G  K  P  C  L
1521   GATGATGGAAGCATTTGGCGGTAAAGGTTATGTTGCCAATACTCCAGCAGAACTGAAAGCTGCTCTGGAAGAAGCTGTTGCTTCCGGCAAACCATGCCTG    1620
       I  N  A  M  I  D  P  D  A  G  V  G  S  G  R  I  K  S  L  N  V  V  S  K  V  G  K  K
1621   ATCAACGCGATGATCGATCCAGACGCTGGTGTCGGAATCTGGCCGTATCTCAAGAGCCTGAACGTTGTAAGTTGGCAAGAAATAATTAGCCAACTTT    1720
                                                                                    1705
1721   GATGACCGGTTACGACCGGTCACATAAAGTGTTCGAATGCCCTTCAAGTTTACTTGAAGGGCATTTTTTTACCTTGCAGTTTATAAACAGGAAAAATTGT    1820
       1758
1821   ATTCAGAGCGGAAAAGCAGATTTAAGCCACGAGAAACATTCTTTTTTATTGAAAATTGCCATAAACACATTTTAAAGCTGGCTTTTT    1908
```

GROUP I STRAINS

GROUP II STRAINS

MATERIALS AND METHODS FOR DETECTION OF OXALOBACTER

CROSS-REFERENCE TO A RELATED APPLICATION

This application is a continuation-in-part of co-pending patent application Ser. No. 08/493,197, filed Jun. 20, 1995, which is a continuation-in-part of patent application Ser. No. 08/262,424, filed Jun. 20, 1994 U.S. Pat. No. 5,604,111.

This invention was made with government support under National Institutes of Heath Grant No. DK 20586. The government has certain rights in this invention.

BACKGROUND OF THE INVENTION

The present invention relates to novel assay methods and devices for determining the presence or concentration of oxalate in a sample. The present invention further relates to the cloning, sequencing and expression of formyl-CoA transferase, an enzyme used in the novel assay for the detection of oxalate. The present invention also relates to novel materials and methods for the detection of *Oxalobacter formigenes* in a sample.

Oxalic acid (Oxalate) is a highly toxic natural by-product of catabolism in vertebrate animals and many consumable plants. Unfortunately, a significant portion of humans are unable to properly metabolizing oxalate, a condition which may result in the formation of kidney stones in those persons. It is estimated that 70% of all kidney stones are composed of some amount of oxalate. Approximately 12 percent of the U.S. population will suffer from a kidney stone at some time in their lives, and the incidence is rising not only in the United States, but also in Sweden and Japan (Curhan, 1993). Moreover, although a healthy person breaks down or excretes sufficient quantities of oxalate to avoid excessive accumulation of oxalate in the tissues, a number of disease states are known to be associated with malfunctions of oxalate metabolism, including pyridoxine deficiency, renal failure and primary hyperoxaluria, a metabolic genetic disorder that results in the excessive deposition of oxalate in the kidneys.

Persons suffering from and at risk for developing kidney stones, as well as patients with lipid malabsorption problems (e.g., sprue, pancreatic insufficiency, inflammatory intestinal disease, bowel resection, etc.), tend to have elevated levels of urinary oxalate, a fact that has been exploited as a means for identifying individuals at risk. While elevated levels of oxalate may be present in urine, detecting elevated levels of oxalate in serum has not been routine due to the difficulty in detecting the low levels of oxalate present in serum.

Most previous methods for measuring oxalate in a biological sample first require the isolation of the oxalate by precipitation, solvent extraction, or an ion-exchange absorption (Hodgkinson, 1970). Quantitation of the isolated oxalate may be determined by any one of several methods including colorimetry, fluorometry, gas-liquid chromatography or isotope dilution techniques. Because many of the oxalate isolation techniques used in these analytical methods are not quantitative, it is normally necessary to correct for the low recovery of oxalate by adding a $^{14}$C-labeled oxalic acid internal standard, which further complicates the analytical method. All these methods are laborious, and consequently expensive because of the amount of skilled laboratory technician time which must be employed. In addition, isolation of the oxalate may require relatively large sample volumes for starting material.

Recently, several advances in the detection and quantitation of oxalate have been made through the use of (a) oxalate degrading enzymes and (b) high performance liquid chromatography. One commercially-available enzymatic test (Sigma Chemical Company, St. Louis, Mo.) employs oxalate oxidase to oxidize oxalate to carbon dioxide and hydrogen peroxide. The hydrogen peroxide produced can then be measured colorimetrically in a second enzymatic reaction in the presence of peroxidase.

In another enzymatic method for measuring oxalate, oxalate decarboxylase is used to convert oxalate to carbon dioxide and formate. The resultant carbon dioxide can be measured manometrically, by the pH change in a carbon dioxide trapping buffer or by the color change in a pH indicator buffer. Whatever method of carbon dioxide assay is adopted, the time required for diffusion and equilibration of carbon dioxide is much longer than is desirable for a rapid analytical method.

Alternatively, the formate produced by the action of oxalate decarboxylase can be assayed with formate dehydrogenase in an NAD/NADH coupled reaction, as described in Costello, 1976 and Yriberri, 1980. This method is both cumbersome and time-consuming because oxalate decarboxylase and formate dehydrogenase differ in their optimum pH requirements, thus necessitating a pH adjustment during the analysis.

Another commercially available enzymatic test (Boehringer Mannheim) cleaves oxalate to formate and carbon dioxide, then oxidizes the formate to bicarbonate by NAD in the presence of the enzyme formate dehydrogenase. The amount of NADH is determined by means of its absorbance at 334, 340, or 365 nm. Another test ("STONE RISK" by Mission Pharmacal) measures oxalate as a part of a battery of tests for kidney stones.

*Oxalobacter formigenes* is a recently discovered, oxalate-degrading obligately anaerobic bacterium residing primarily in the intestines of vertebrate animals, including man (Allison et al., 1986). This bacterium is unique among oxalate-degrading organisms having evolved a total dependence on oxalate metabolism for energy (Dawson et al., 1980). Recent evidence suggests that *Oxalobacter formigenes* has an important symbiotic relationship with vertebrate hosts by regulating oxalic acid absorption in the intestine as well as oxalic acid levels in the plasma (Hatch and Freel, 1996). Studies by Jensen and Allison (1994) comparing various *O. formigenes* isolates revealed only limited diversity of their cellular fatty acids, proteins, and nucleic acid fragments. Based on these comparisons, strains of *O. formigenes* have been divided into two major subgroups. Special conditions are required to culture *O. formigenes* and their detection is based generally on the appearance of zones of clearance of calcium oxalate crystals surrounding colonies (Allison et al., 1986).

As illustrated above, the currently existing assays for oxalate suffer from numerous problems, including cost, inaccuracy, reliability, complexity, and lack of sensitivity. Accordingly, it is an object of the subject invention to provide a simple, accurate, and sensitive assay for the detection of low levels of oxalate in a biological sample.

The current methods for culturing and identifying the presence of *Oxalobacter formigenes* are technically demanding and time consuming, and therefore, are not suitable for rapid and specific identification of *O. formigenes*, particularly for clinical diagnostics. Accordingly, another object of the subject invention is to provide a rapid, accurate polynucleotide probe-based assay for the detection of *O. formigenes*.

BRIEF SUMMARY OF THE INVENTION

The subject invention concerns the cloning, sequencing, and expression of the formyl-CoA transferase (frc) and the oxalyl-CoA decarboxylase (oxc) genes of *Oxalobacter formigenes*, and the use of the enzymes to detect the presence of oxalate in a sample. The assay of the subject invention provides, for the first time, a rapid, sensitive method to detect even very low concentrations of oxalate in biological samples. Advantageously, the biological samples in which oxalate can be detected include both urine and serum samples. The enzyme system used according to the subject invention converts oxalate to carbon dioxide and formate. In a preferred embodiment of the subject invention, the production of formate is then measured colorimetrically. This assay provides a sensitive, accurate and convenient means for detecting oxalate.

A further aspect of the subject invention is the discovery of the *O. formigenes* genes which encode the formyl-CoA transferase and the oxalyl-CoA decarboxylase enzymes. The discovery of these genes makes it possible to efficiently produce large quantities of pure formyl-CoA transferase and oxalyl-CoA decarboxylase for use in the assay of the subject invention or other appropriate application.

The subject invention further concerns a dipstick device for the detection and quantitation of oxalate in a sample. The dipstick device comprising comprises the oxalyl-CoA decarboxylase and formyl-CoA transferase enzymes of the present invention immobilized on a carrier matrix. A detectable signal is generated on the dipstick if oxalate is present in the sample.

The subject invention also provides a means for detecting the presence of *Oxalobacter formigenes* organisms in a sample. The method of detection provided for herein involves polynucleotide probes which can be used to identify *Oxalobacter formigenes*.

The subject invention also concerns the polynucleotide primers and the use thereof for polymerase chain reaction (PCR) amplification of *Oxalobacter formigenes* nucleotide sequences. Amplified Oxalobacter sequences can then be detected using the polynucleotide probes of the subject invention.

BRIEF DESCRIPTION OF THE DRAWINGS

FIGS. 2A–2B show the nucleotide sequence of the formyl-CoA transferase gene and the deduced amino acid sequence of the formyl-CoA transferase polypeptide from *Oxalobacter formigenes*.

FIGS. 3A–3B show the nucleotide sequence of the oxalyl-CoA decarboxylase gene and flanking regions from *Oxalobacter formigenes*. The consensus ribosome-binding site lies approximately 10 bases upstream (double-underlined letters) from the putative translation initiation codon (positions 1 to 3). A rho-independent termination sequence lies at positions 1758 to 1790 (double-underlined letters). A putative TPP-binding site appears between positions 1351 and 1437.

BRIEF DESCRIPTION OF THE SEQUENCES

Figure 1A:
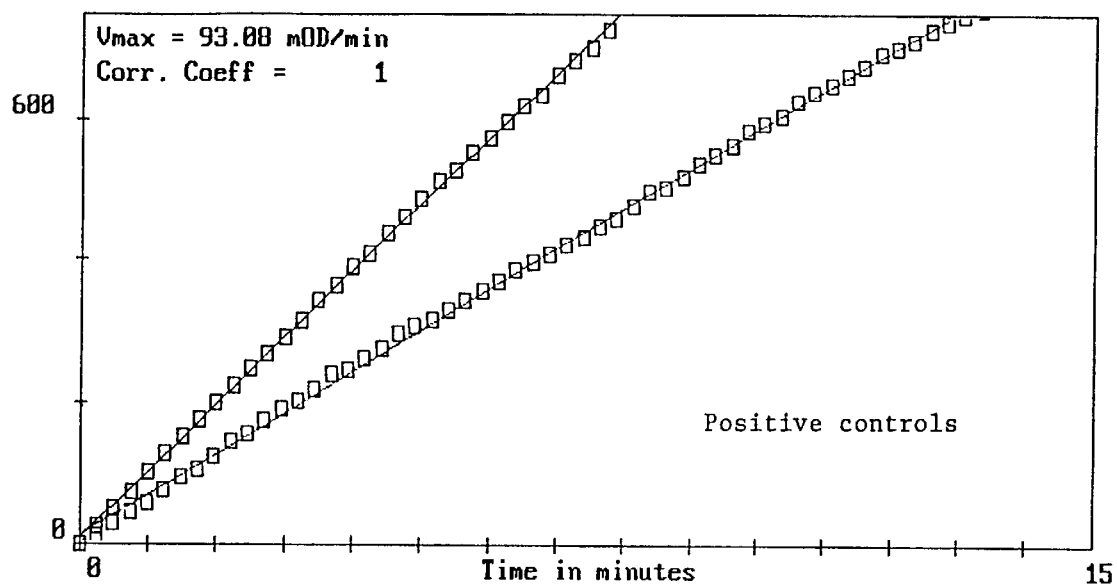
FIGS. 1A–1E show the detection of varying concentrations of oxalate in a sample. Colorimetric absorbance for each sample was plotted over time (minutes). Positive and negative control panels are also shown.
Figure 1B:
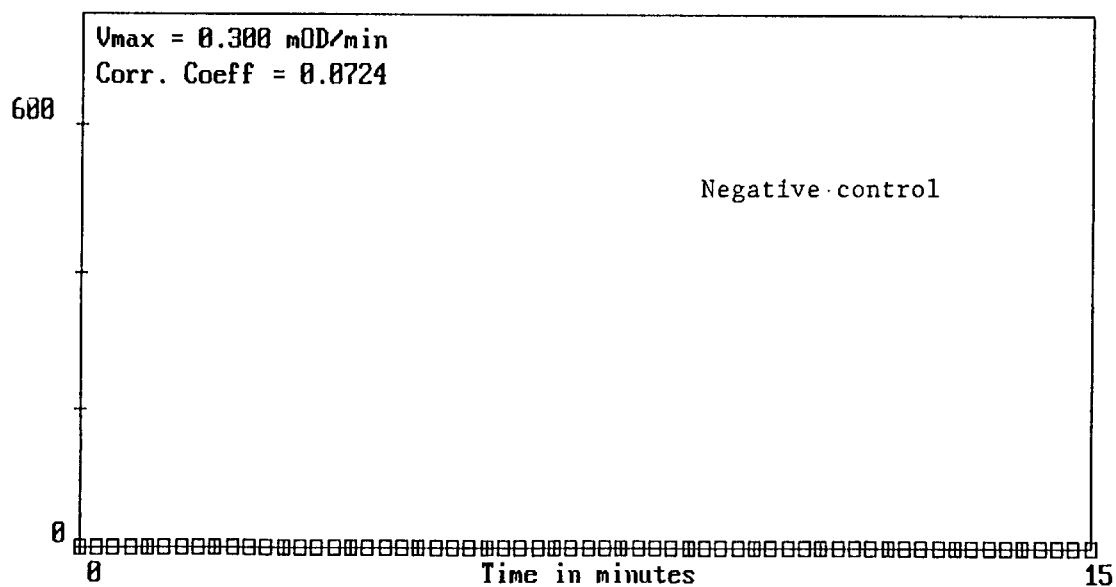
Figure 1C:
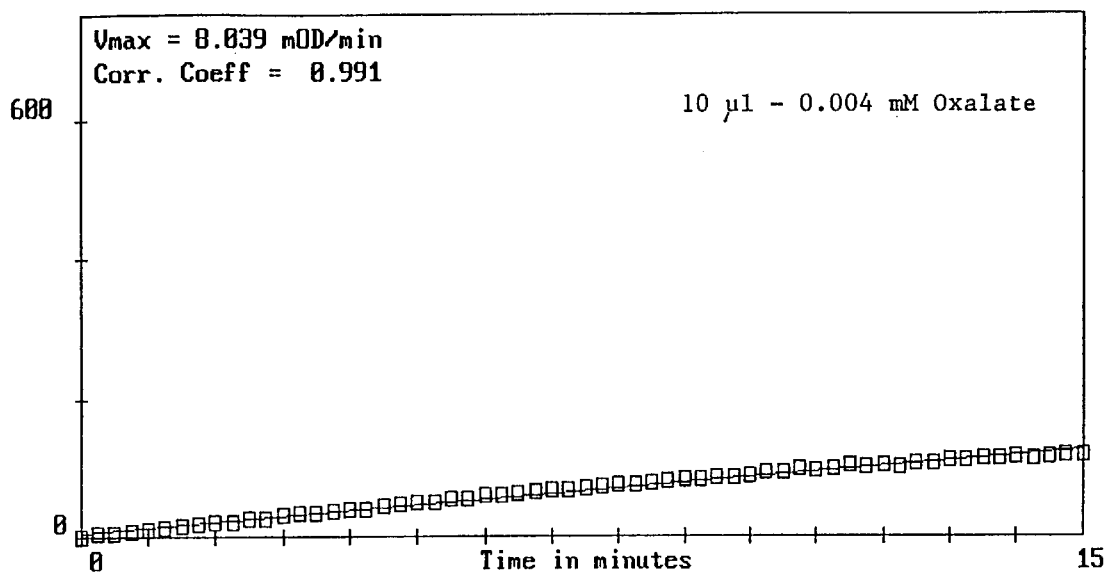
Figure 1D:
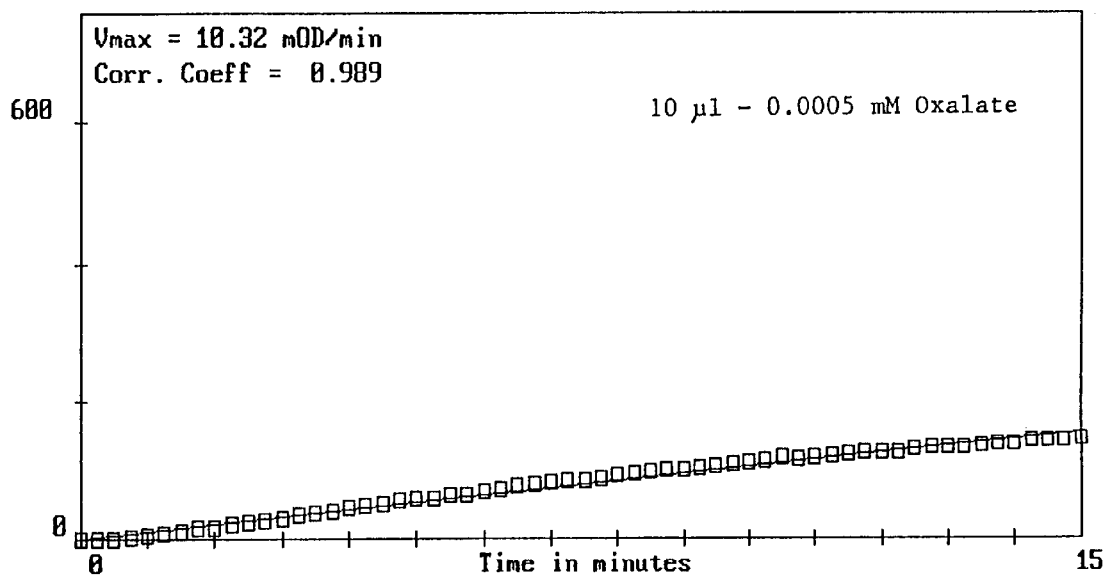
Figure 1E:
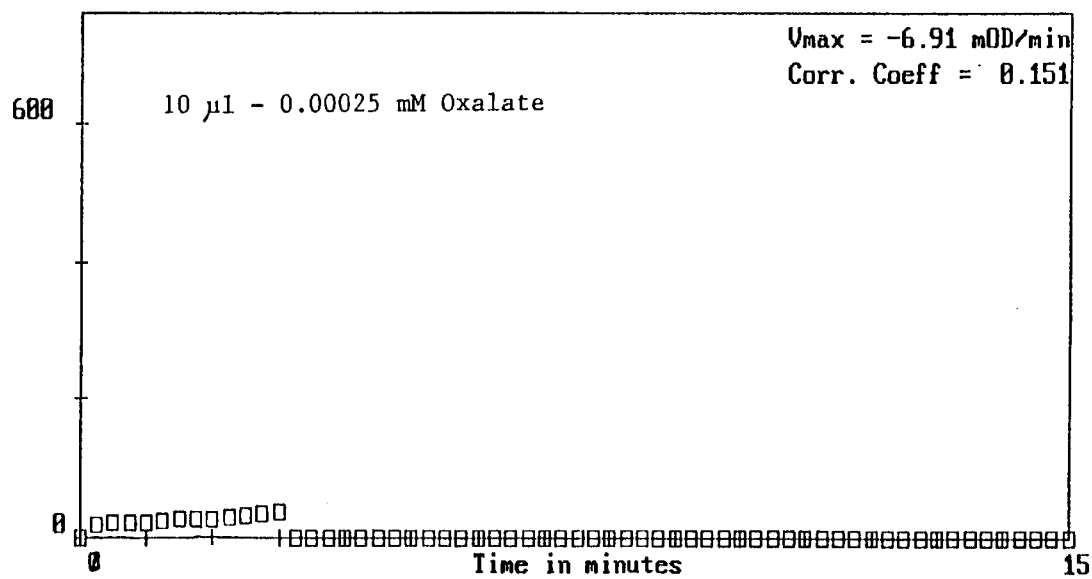

SEQ ID NO. 1 is a nucleotide sequence for the formyl-CoA transferase gene (also shown in FIGS. 2A–2B).

SEQ ID NO. 2 is a polypeptide encoded by SEQ ID NO. 1, which can be used according to the subject invention.

SEQ ID NO. 3 is the nucleotide sequence for the oxalyl-CoA decarboxylase gene (also shown in FIGS. 3A–3B).

SEQ ID NO. 4 is a polypeptide encoded by SEQ ID NO. 3, which can be used according to the subject invention.

SEQ ID NO. 5 is an oxalyl-CoA decarboxylase sequence, which can be used as a probe according to the subject invention.

SEQ ID NO. 6 is an oxalyl-CoA decarboxylase sequence, which can be used as a probe or PCR primer according to the subject invention.

SEQ ID NO. 7 is an oxalyl-CoA decarboxylase 5'-primer, which can be used according to the subject invention.

SEQ ID NO. 8 is an oxalyl-CoA decarboxylase 3'-primer, which can be used according to the subject invention.

SEQ ID NO. 9 is an oxalyl-CoA decarboxylase sequence, which can be used as a probe according to the subject invention.

SEQ ID NO. 10 is a formyl-CoA transferase sequence, which can be used as a probe according to the subject invention.

SEQ ID NO. 11 is an oxalyl-CoA decarboxylase sequence, which can be used as a PCR primer according to the subject invention.

DETAILED DESCRIPTION OF THE INVENTION

The subject invention provides an accurate, sensitive assay for oxalate in biological samples such as urine and serum. Elevated levels of oxalate are correlated with urinary tract stone formation, as well as other health problems. Early detection of high levels of oxalate makes it possible to prevent, delay or reduce adverse health consequences through appropriate medication and through modulation of diet.

In the presently described diagnostic system, two enzymes are used to catabolize oxalate to carbon dioxide and formate. Specifically, any oxalate that may be present in a sample being assayed is converted into formate and carbon dioxide ($CO_2$) through the combined action of the enzymes oxalyl-CoA decarboxylase and formyl-CoA transferase. The formate can then be detected using a variety of techniques known in the art. In a preferred embodiment, the production of formate is measured colorimetrically by linking the catabolism of formate with the production of a detectable color change (for example, the formation of a compound that absorbs a particular wavelength of light). The production of formate is directly correlated with the amount of oxalate present in the sample. Therefore, if a known amount of formate is produced using the subject enzyme system, then the amount of oxalate present in the sample can be easily quantitated.

In a preferred embodiment, the enzymes used in the subject invention are expressed by genes from the bacterium *Oxalobacter formigenes*. The genes encoding both oxalyl-CoA decarboxylase (Lung, 1994) and formyl-CoA transferase enzymes have been cloned and expressed, thus providing a readily-available source of reagent material. The subject assay is capable of detecting oxalate levels in a range as low as 0.00025–0.0005 mM (FIGS. 1A–1E). This level of sensitivity makes the subject assay capable of direct detection of oxalate in serum samples consisting of little as 10 μl volume. The described system can be easily automated with standard systems known in the art.

In a preferred embodiment of the subject assay, the enzymatic reaction can be carried out in the wells of flat-bottomed 96-well microtiter plates and read in an automated plate reader. Suitable concentrations of the assay reagents oxalyl-CoA decarboxylase, oxalyl-CoA, β-NAD, formate dehydrogenase, and the sample to be assayed are added to the microtiter wells. The reaction is then brought to equilibrium (two minute incubation at 37° C. in the plate reader) to permit degradation of any residual formate that may be present in the sample. The formyl-CoA transferase enzyme is then added to the mixture to start the reaction, and the plate is read at 15 second intervals. Formate production is determined by measuring the reduction in NAD in the presence of formate dehydrogenase by detecting changes in absorbance of the sample at 340 nm (Baetz and Allison, 1989). The quantity of oxalate is determined by comparison of the unknown samples with standards having a known amount of oxalate.

Further, the enzymatic reaction of the subject assay will not be initiated until the formyl-CoA transferase, oxalyl-CoA decarboxylase, and oxalyl-CoA are all present within the reaction mixture. Therefore, initiation of the enzymatic reaction can be prevented by withholding one of the above reagents from the reaction mix. Preferably, oxalyl-CoA decarboxylase and oxalyl-CoA are added first, and the reaction is initiated by the addition of formyl-CoA transferase to the mix. However, the order of addition of the three reagents is not material to the function of the assay, so long as one of the reagents is withheld until just prior to the desired initiation point of the assay.

The formyl-CoA transferase and oxalyl-CoA decarboxylase enzymes used in the subject invention can be obtained and purified as a natural product of *Oxalobacter formigenes* (Baetz and Allison, 1989 and 1990). Alternatively, the enzymes can be obtained from host cells expressing the recombinant polynucleotide molecules of the subject invention that encode the enzymes. Other reagents used in the subject assay can be obtained from conventional sources, such as Sigma Chemical Company, St. Louis, Mo. Further, a person of ordinary skill in the art can readily determine the optimal concentrations of the reagents to use in the assay described herein.

A further aspect of the subject invention concerns the cloning, sequencing and expression of the *Oxalobacter formigenes* gene which encodes the formyl-CoA transferase used in the assay that is a subject of the invention. The gene was cloned using degenerate oligonucleotide probes (based on partial amino acid sequencing of tryptic peptides) to screen an Oxalobacter genomic DNA library. The gene encodes a polypeptide having a molecular weight of approximately 40 kD. The subject invention further concerns the cloning, sequencing, and expression of the gene which encodes oxalyl-CoA decarboxylase from *Oxalobacter formigenes*. The nucleotide sequence of the cDNA of formyl-CoA transferase and oxalyl-CoA decarboxylase are shown in FIGS. 2A–2B and 3A–3B, respectively (SEQ ID NOS. 1 and 3).

Because of the redundancy of the genetic code, a variety of different polynucleotide sequences can encode the formyl-CoA transferase polypeptide disclosed herein. It is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional enzymatic activity of the encoded polypeptide. Further, the subject invention contemplates those polynucleotide molecules having sequences which are sufficiently homologous with the DNA sequences shown in FIGS. 2A–2B and 3A–3B (SEQ ID NOS. 1 and 3) so as to permit hybridization with those sequences under standard high-stringency conditions. Such hybridization conditions are conventional in the art (see, e.g., Maniatis et al., 1989).

As a person skilled in the art would appreciate, certain amino acid substitutions within the amino acid sequence of the polypeptide can be made without altering the functional activity of the enzyme. For example, amino acids may be placed in the following classes: non-polar, uncharged polar, basic, and acidic. Conservative substitutions, whereby an amino acid of one class is replaced with another amino acid of the same class, fall within the scope of the subject invention so long as the substitution does not materially alter the enzymatic reactivity of the polypeptide. Non-conservative substitutions are also contemplated as long as the substitution does not significantly alter the functional activity of the encoded polypeptide.

The polynucleotides of the subject invention can be used to express the recombinant formyl-CoA transferase enzyme. They can also be used as a probe to detect related enzymes. The polynucleotides can also be used as DNA sizing standards.

The polypeptides encoded by the polynucleotides can be used to raise an immunogenic response to the formyl-CoA transferase enzyme. They can also be used as molecular weight standards, or as inert protein in an assay. The polypeptides can also be used to detect the presence of antibodies immunoreactive with the enzyme.

The polynucleotide sequences of the subject invention may be composed of either RNA or DNA. More preferably, the polynucleotide sequences are composed of DNA. The subject invention also encompasses those polynucleotides that are complementary in sequence to the polynucleotide sequences disclosed herein.

Another aspect of the subject invention pertains to kits for carrying out the enzyme assay for oxalate. In one embodiment, the kit comprises, in packaged combination and in relative quantities to optimize the sensitivity of the described assay method, (a) the oxalyl-CoA decarboxylase, oxalyl-CoA, β-NAD, and formate dehydrogenase; and (b) formyl-CoA transferase. The kit may optionally include other reagents or solutions, such as buffering and stabilization agents, along with any other reagents that may be required for a particular signal generation system. Other reagents such as positive and negative controls can be included in the kit to provide for convenience and standardization of the assay method.

The subject invention further concerns a method for detecting the presence of *Oxalobacter formigenes* organisms in a sample. Specific polynucleotide probes can be prepared based on the nucleotide sequence of either the oxalyl-CoA decarboxylase or the formyl-CoA transferase gene sequence of *Oxalobacter formigenes*. The polynucleotide probes of the subject invention can be used to identify *Oxalobacter formigenes* in a sample, and to classify the strain of *Oxalobacter formigenes* detected.

The polynucleotide probes of the subject invention can be used according to standard procedures and conditions to specifically and selectively detect polynucleotide sequences that have sufficient homology to hybridize with the probe. DNA can be isolated from bacterial microorganisms in a biological specimen (e.g., biopsy, fecal matter, tissue scrapings, etc.) using standard techniques known in the art and the isolated DNA screened for hybridization with Oxalobacter oxalyl-CoA decarboxylase-specific and/or formyl-CoA transferase-specific polynucleotide probes. Various degrees of stringency can be employed during the hybridization, depending on the amount of probe used for hybridization, the level of complementarity (i.e., homology) between the probe and target DNA fragment to be detected. The degree of stringency can be controlled by temperature, ionic strength, pH, and the presence of denaturing agents such as formamide during hybridization and washing. Hybridization methods and conditions are known in the art and are generally described in *Nucleic Acid Hybridization: A Practical Approach* (Hames, B. D., S. J. Higgins, eds.), IRL Press (1985).

The polynucleotide probes of the subject invention include, for example, the oxalyl-CoA decarboxylase probe A (SEQ ID NO. 5), probe AP15 (SEQ ID NO. 6), and probe AP34 (SEQ ID NO. 9) specifically exemplified herein. Probes for formyl-CoA transferase include, for example, probe AP273 (SEQ ID NO. 10) specifically exemplified herein. The nucleotide sequences of the exemplified probes are shown below:

Probe A 5'-GAGCGATACCGATTGGA-3' (SEQ ID NO. 5)
Probe AP15 5'-GCACAATGCGACGACGA-3' (SEQ ID NO. 6)
Probe AP34 5'-ATACTCGGAATTGACGT-3' (SEQ ID NO. 9)
Probe AP273 5'-TTCATGTCCAGTTCAATCGAACG-3' (SEQ ID NO. 10)

The polynucleotide probes contemplated in the subject invention also include any polynucleotide molecule comprising a nucleotide sequence capable of specifically hybridizing with oxalyl-CoA decarboxylase or formyl-CoA transferase polynucleotide sequences disclosed herein. As used herein, reference to "substantial homology" or "substantially complementary" refers not only to polynucleotide probes of the subject invention having 100% homology with the nucleotide sequence of the target gene, or fragments thereof, but also to those sequences with sufficient homology to hybridize with the target gene. Preferably, the degree of homology will be 100%; however, the degree of homology required for detectable hybridization will vary in accordance with the level of stringency employed in the hybridization and washes. Thus, probes having less than 100% homology to the oxalyl-CoA decarboxylase or formyl-CoA transferase polynucleotide sequences can be used in the subject method under appropriate conditions of stringency. In a preferred embodiment, high stringency conditions are used. In addition, analogs of nucleosides may be substituted for naturally occurring nucleosides within the polynucleotide probes. Such probes having less than 100% homology or containing nucleoside analogs are within the scope of the subject invention. The skilled artisan, having the benefit of the disclosure contained herein, can readily prepare probes encompassed by the subject invention.

In addition, the subject invention also concerns polynucleotide primers that can be used for polymerase chain reaction (PCR) amplification of *Oxalobacter formigenes* nucleotide sequences. PCR amplification methods are well known in the art and are described in U.S. Pat. Nos. 4,683,195; 4,683,202; and 4,800,159. In a preferred embodiment, the polynucleotide primers are based on the oxalyl-CoA decarboxylase or formyl-CoA transferase gene sequence and can be used to amplify the full length or a portion of the target gene. The amplified Oxalobacter sequences can be detected using the probes of the subject invention according to standard procedures known in the art.

The polynucleotide primers of the subject invention include, for example, oxalyl-CoA decarboxylase PCR primer 1 (SEQ ID NO. 7), PCR primer 2 (SEQ ID NO. 8), PCR primer AP15 (SEQ ID NO. 6), and PCR primer AP22 (SEQ ID NO. 11), specifically exemplified herein. The nucleotide sequences of the exemplified PCR primers are shown below:

PCR primer 1 5'-CAGGTTATGCAGTTCT-3' (SEQ ID NO. 7)
PCR primer 2 5'-GGATGGTTGTCAGGCAG-3' (SEQ ID NO. 8)
PCR primer AP15 5'-GCACAATGCGACGACGA-3' (SEQ ID NO. 6)
PCR primer AP22 5'-GTAGTTCATCATTCCGG-3' (SEQ ID NO. 11)

The skilled artisan, having the benefit of the disclosure contained herein, can readily prepare other primers of varying nucleotide length and sequence that can be used to amplify all or portions of the oxalyl-CoA decarboxylase and/or the formyl-CoA transferase gene.

The polynucleotide probes and primers of the subject invention can be chemically synthesized or prepared through recombinant means using standard methods and equipment. The polynucleotide probes and primers can be in either single- or double-stranded form. If the probe or primer is double-stranded, then single-stranded forms can be prepared from the double-stranded form. The polynucleotide probes and primers may be comprised of natural nucleotide bases or known analogs of the natural nucleotide bases. The probes and primers of the subject invention may also comprise nucleotides that have been modified to bind labeling moieties for detecting the probe or primer or amplified gene fragment.

The polynucleotide molecules of the subject invention can be labeled using methods that are known in the art. The polynucleotides may be radioactively labeled with an isotope such as $^3H$, $^{35}S$, $^{14}C$, or $^{32}P$. The polynucleotides can also be labeled with fluorophores, chemiluminescent compounds, or enzymes. For example, a polynucleotide molecule could be conjugated with fluorescein or rhodamine, or luciferin or luminol. Similarly, the polynucleotide molecule can be conjugated with an enzyme such as horseradish peroxidase or alkaline phosphatase. Polynucleotide molecules can also be detected by indirect means. For example, the polynucleotide may be conjugated with ligands, haptens, or antigenic determinants. The conjugated polynucleotide is then contacted with the ligand receptor, with an anti-ligand molecule that binds to the ligands, or with an antibody that binds to the hapten/antigenic determinant, respectively. For example, the polynucleotide can be labelled with digoxygenin and detected with labelled anti-digoxygenin antibodies. The ligand receptor, anti-ligand molecule, or antibody may be directly labeled with a detectable signal system, such as a fluorophore, chemiluminescent molecule, radioisotope, or enzyme. Methods for preparing and detecting labeled moieties are known in the art.

In one embodiment of the present detection method, samples to be tested for the presence of *Oxalobacter formigenes* are obtained from a person or animal, and DNA is isolated from the specimen using standard techniques known in the art. For example, cells can be lysed in an alkali solution, the nucleic acid extracted in phenol:chloroform, and then precipitated with ethanol. The DNA is then fragmented into various sizes using restriction endonuclease enzymes or other means known in the art. The DNA fragments are then electrophoretically separated by size on an agarose gel. In an alternative embodiment, the DNA fragments are subjected to PCR amplification using PCR primers of the present invention prior to gel electrophoresis in order to specifically amplify portions of the formyl-CoA transferase and oxalyl-CoA decarboxylase genes.

After the DNA fragments are separated on the gel, the size-fractionated DNA fragments are transferred to a membrane matrix, such as nitrocellulose, nylon, or polyvinylidene difluoride (PVDF), by Southern blotting. The DNA immobilized on the membrane matrix is single-stranded. Polynucleotide probes of the subject invention are then contacted with the membrane and allowed to hybridize with the DNA immobilized on the membrane. A probe of the present invention can be labeled with a detectable signal, such as a radioisotope, or the probe can be labeled with a hapten or antigen such as digoxigenin. The hybridization can be performed under conditions known in the art. After hybridization of the probe with the DNA fragments on the membrane, the membrane is washed to remove non-hybridized probe. Standard wash conditions are known in the art, and the stringency and number of washes employed can vary.

The membrane is then tested or observed for the presence of hybridized probe. For example, if the hybridized probe was labeled with a hapten or antigen, then it can be detected using an antibody that binds to the conjugated hapten or antigen on the probe. The antibody can be directly labeled with a detectable fluorophore, chemiluminescent molecule, radioisotope, enzyme, or other signal generating system known in the art. Alternatively, the antibody can be detected using a secondary reagent that binds to the antibody, such as anti-immunoglobulin, protein A, protein G, and other antibody binding compositions known in the art. The secondary reagent can be labeled with a detectable fluorophore, chemiluminescent molecule, radioisotope, or enzyme. The presence of a detectable hybridization signal on the membrane indicates the presence of *Oxalobacter formigenes* in a test sample.

The subject invention also concerns a kit for the detection of *Oxalobacter formigenes* in a sample. A kit contemplated by the subject invention may include in one or more containers: polynucleotide probes, positive and negative control reagents, and reagents for detecting the probes. The kit may also include polynucleotide primers for performing PCR amplification of specific *Oxalobacter formigenes* genes. In a preferred embodiment, the polynucleotide probes and primers are specific for the oxalyl-CoA decarboxylase and formyl-CoA transferase genes of *O. formigenes*.

The subject invention also concerns a dipstick device comprising the enzymes of the subject invention and dyes and/or substrates immobilized on a carrier matrix. Any dye or substrate that yields a detectable product upon exposure to the reaction products that are produced by the enzymatic reaction of oxalate with oxalyl-CoA decarboxylase and formyl-CoA transferase as described herein is contemplated for use with the subject dipstick device. The carrier matrix of the assay device can be composed of any substance capable of being impregnated with the enzyme and dye components of the subject invention, as long as the matrix is substantially inert with respect to the analyte being assayed for. For example, the carrier matrix may be composed of paper, nitrocellulose, PVDF, or plastic materials and the like.

Incorporation of the enzymes, dye and other components on the carrier matrix can be accomplished by any method such as dipping, spreading or spraying. A preferred method is impregnation of the carrier matrix material by dipping in a reagent solution and drying to remove solvent. Drying can be accomplished by any means which will not deleteriously affect the reagents incorporated, and typically is by means of an air drying oven.

The dipstick device of the subject invention is dipped in or contacted with a sample to be tested for the presence or amount of oxalate. Positive and negative controls can be used in conjunction with the dipstick device. An appropriate amount of time is allowed to pass and then the dipstick is assessed for a positive reaction by visual inspection. If oxalate is present in the sample then a detectable signal, usually in the form of a color, can be observed on the dipstick. Typically, the intensity of the color developed in a fixed time period is proportional to the concentration of oxalate present in the sample.

Following are examples which illustrate procedures, including the best mode, for practicing the invention. These examples should not be construed as limiting. All percentages are by weight and all solvent mixture proportions are by volume unless otherwise noted.

EXAMPLE 1

Determination of Level of Sensitivity of Enzyme Assay System

Samples containing oxalate at concentrations ranging from 0.004 mM to 0.00025 mM were prepared in 10 µl volumes. The samples were then assayed using the enzyme system of the subject invention in 96-well microtiter plates. Reagents were then added at the following concentrations: $KH_2PO_4$ (pH 6.7), 50 mM; $MgCl_2$, 5 mM; thiamine PPi (TPP), 2 mM; oxalyl-CoA, 0.375 mM; β-NAD, 1.0 mM; formate dehydrogenase, 0.25 IU; and oxalyl-CoA decarboxylase, 0.03 U. The reaction mixture was then incubated at 37° C. for 2 minutes in order to permit the degradation of any residual formate that may be present in the sample mixture. The reaction was then initiated by the addition of formyl-CoA transferase to the sample mixture. Changes in $A_{340}$ were measured every 15 seconds at 37° C. (FIGS. 1A–1E). Appropriate positive and negative controls were run simultaneously with the assay.

EXAMPLE 2

Detection of *Oxalobacter formigenes* in a Sample

Strains of *Oxalobacter formigenes* used in the following methods are listed in Table 1 below.

TABLE 1

Description of the *Oxalobacter formigenes* strains

| Group Classification of *O. formigenes* strains[a] | Strain | Source of Isolate |
| --- | --- | --- |
| Group I | OxB | Sheep rumen |
|  | OxWR | Wild rat cecum |
|  | SOx-4 | Freshwater lake sediment |
|  | SOx-6 | Freshwater lake sediment |
|  | POxC | Pig cecum |
|  | HC-1 | Human feces |
| Group II | BA-1 | Human feces |
|  | OxK | Human feces |
|  | HOxBLS | Human feces |
|  | HOxRW | Human feces |
|  | OxCR | Lab rat cecum |
|  | OxGP | Guinea pig cecum |

[a]From Jensen and Allison (1994).

All *Oxalobacter formigenes* strains were grown in medium B containing 30 mM oxalate, as described in Allison et al. (1985). Human fecal samples (approximately 60 mg) were inoculated anaerobically into vials containing 9 ml of media B, then sequentially transferred through $10^{-8}$ dilutions. Cultures were incubated at 37° C. for 10 days and biochemically tested for the catabolic consumption of oxalate by $CaCl_2$ precipitation (50 µl media, 100 µl 1% $CaCl_2$, and 2.7 ml $dH_2O$) and spectrophotometric analyses (600 nm).

Cultures (10–15 ml) of *O. formigenes* were centrifuged at 10,000×g, the bacterial pellet was resuspended in 567 µl TE buffer (10 mM Tris-Cl, pH 7.5 plus 1 mM EDTA, pH 8.0), 30 µl 10% sodium dodecyl sulfate (SDS) and 3 µl of proteinase K (20 mg/ml), and the mixture incubated 5 hr at 37° C. to ensure bacterial cell lysis. Nucleic acids were extracted from the lysates using phenol/chloroform/isoamylalcohol (25:24:1). Chromosomal DNA was precipitated from the aqueous phase by adding ½ volume of 7.5 M ammonium acetate and 2 volumes of 100% ethanol. DNA was recovered by centrifugation (12,000×g), washed once with 70% ethanol, and the pellet resuspended in 15–20 µl $H_2O$. Bacterial DNA was also isolated directly from fresh human stool samples following lysis with chaotropic salt and guanidine thiocyanate, then binding to glass matrix (GlasPac, National Scientific Supply, San Rafael, Calif.) (Stacy-Phips et al., 1995).

Bacterial DNA was digested with the restriction endonuclease Hind III (Life Technologies, Inc., Gaithersburg, Md.). The restriction-enzyme generated fragments were size separated by gel electrophoresis through 0.5% agarose, stained with ethidium bromide (EtBr), illuminated with UV light, and photographed to document proper digestion. Digested DNA was then transferred from the agarose gels to positively-charged nylon membranes (Boehringer-Mannheim GmBH, Indianapolis, Ind.) by positive pressure blotting and UV cross-linking (Stratagene, LaJolla, Calif.). Hybridizations were carried out using internal sequence oligonucleotide probes. Oligonucleotides were synthesized in the University of Florida ICBR Oligonucleotide Synthesis Laboratory (Gainesville, Fla.) and have the sequences:

AP15 5'-GCACAATGCGACGACGA-3' (SEQ ID NO. 6)
AP22 5'-GTAGTTCATCATTCCGG-3' (SEQ ID NO. 11)
AP34 5'ATACTCGGAATTGACGT-3' (SEQ ID NO. 9)
AP273 5'-TTCATGTCCAGTTCAATCGAACG-3' (SEQ ID NO. 10).

Each oligonucleotide was end-labeled with digoxigenin in a reaction using terminal transferase. The digoxigenin-labeled oligonucleotide probes were hybridized to the immobilized DNA fragments and hybridization detected colorimetrically by enzyme-linked immunoassay (ELISA) using an anti-digoxigenin alkaline phosphatase conjugate according to the manufacturer's protocol provided with the GENIUS III detection system (Boehringer-Mannheim).

All PCRs were performed according to protocols described in Anderson et al. (1993). Briefly, 50 µl reactions contained 1.5 mM $MgCl_2$, 200 µM dNTP, 1.25 U Taq polymerase (GIBCO-BRL, Bethesda, Md.), 1 µg template DNA and 1 µM each of a 5' and 3' primer. A preferred reaction profile proved to be 94° C. for 5 min, then 45 cycles of 94° C. for 1 min of denaturation, 55° C. for 2 min of annealing and 72° C. for 3 min of primer extension. PCR products were size separated by gel electrophoresis in 1.2% agarose containing EtBr and photographed in UV light. PCR primer AP15 (SEQ ID NO. 6) and primer AP22 (SEQ ID NO. 11) were used as primers.

Figures 4A, 4B, 4C:
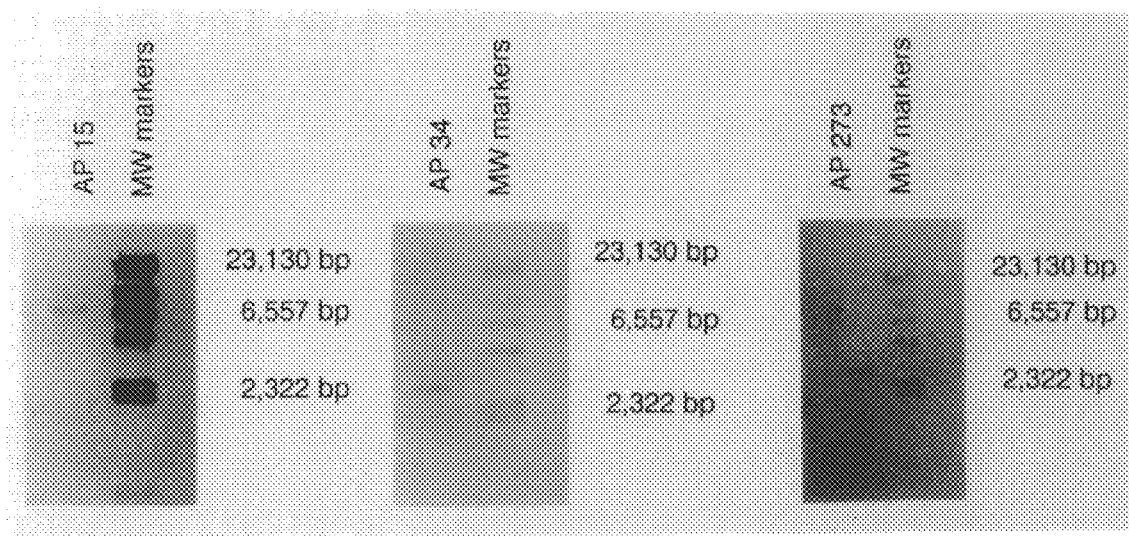
FIGS. 4A–4C show an RFLP analysis of *O. formigenes*, strain OxB using probes specific for the oxc gene encoding oxalyl-CoA decarboxylase and the frc gene encoding formyl-CoA transferase. Genomic DNA isolated from a 14 day culture of *O. formigenes* strain OxB was digested with the restriction enzyme HIND III. The digested DNA was size fractionated by electrophoreses through 0.5% agarose gels, electroblotted to a nylon membrane, then hybridized with either probe AP15 (SEQ ID No. 6) or probe AP34 (SEQ ID NO. 9) to detect oxc or probe AP273 (SEQ ID NO. 10) to detect frc.

Previous studies by Lung et al. (1994) showed that genomic DNA of *O. formigenes*, strain OxB, could be digested with the restriction enzyme Hind III and that a limited number of enzyme cleavage sites existed near or within the oxalyl-CoA decarboxylase (oxc) gene. A RFLP analysis of Hind III digested OxB genomic DNA using either probe AP15 (SEQ ID NO. 6), a probe homologous to an internal sequence of the oxc gene, probe AP34 (SEQ ID NO. 9), a probe homologous to a 5'-end sequence of the oxc gene but separated from the probe AP15 (SEQ ID NO. 6) sequence by a Hind III site, or probe AP273 (SEQ ID NO. 10), a probe homologous to an internal sequence of the formyl-CoA transferase (frc) gene, is shown in FIGS. 4A–4C. Using probe AP15 (SEQ ID NO. 6), a fragment of approximately 7 kb containing a portion of the oxc gene was detected, while fragments of approximately 3 kb were detected using either probe AP34 (SEQ ID NO. 9) or probe AP273 (SEQ ID NO. 10). The 3 kb fragment identified by probe AP34 (SEQ ID NO. 9) is distinct from the 3 kb fragment detected by probe AP273 (SEQ ID NO. 10).

Figures 5A, 5B:
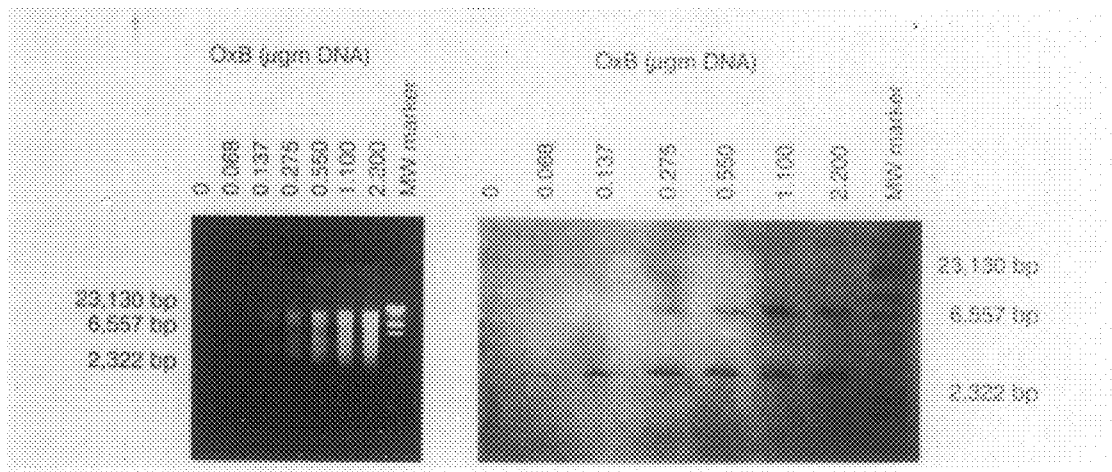
FIGS. 5A–5D show the sensitivity of detecting the oxc and frc genes in RFLP of *O. formigenes* strain OxB versus strain HC-1. Genomic DNA from each of the two strains was digested with the restriction enzyme HIND III. Two-fold serial dilutions were made of the digested DNA and size fractionated by electrophoresis through 0.5% agarose gels (left panels). RFLP analyses were carried out as described in FIGS. 4A–4C, except the nylon membranes were hybridized with a 1:1 mixture of probe AP15 (SEQ ID NO. 6) plus probe AP273 (SEQ ID NO. 10) (right panels).
Figures 5C, 5D:
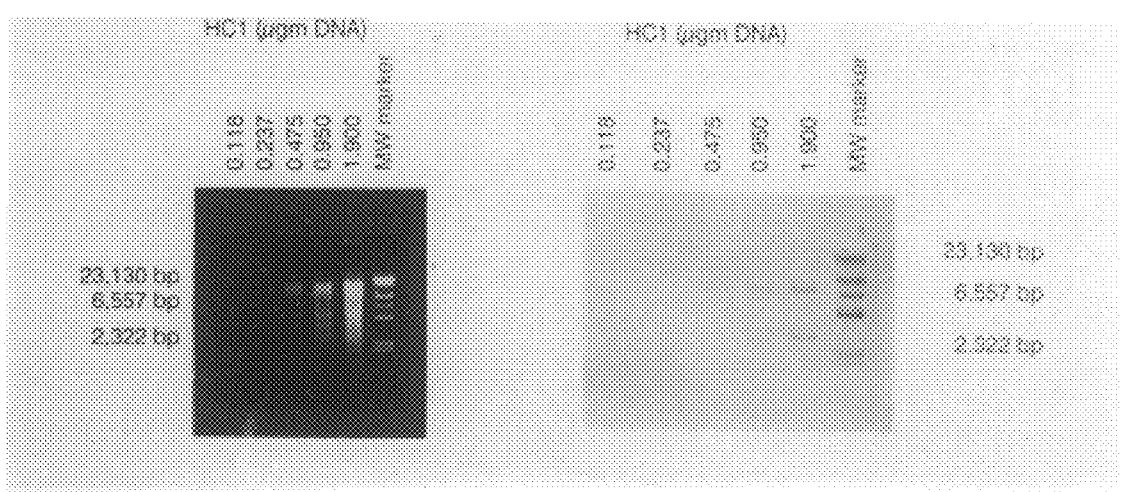

As shown in FIGS. 5A–5D, the oxalyl-CoA decarboxylase and formyl-CoA transferase genes were consistently detected in samples containing as little as 0.06 to 0.20 µg of *O. formigenes*, strain OxB, DNA or approximately 0.20 to 0.40 µg of *O. formigenes* DNA from other group I strains, such as HC-1. The 23-bp probe AP273 (SEQ ID NO. 10) can detect the frc gene in DNA samples containing only one-fourth the amount of DNA required for the 13 bp probe AP15 (SEQ ID NO. 6) to detect the oxc gene (FIGS. 5A–5B, upper panel). These probes are highly specific for *O. formigenes* since they fail to bind to other bacterial DNA, including *Escherichia coli*, *Alcaligenes oxalaticus*, and fecal bacteroides.

Figure 6:
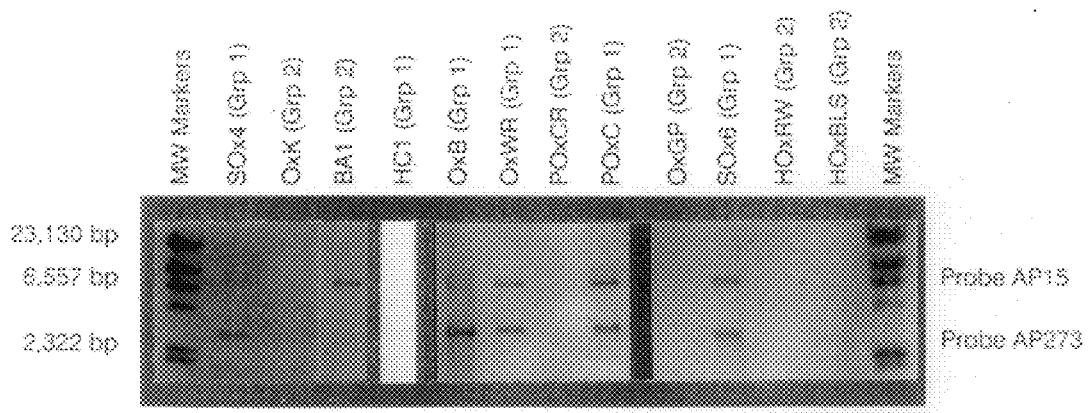
FIG. 6 shows the detection of the oxc and frc genes in various strains of *O. formigenes* by RFLP analysis. RFLP was carried out as described in FIGS. 5A–5D.

Protein, lipid and genetic studies of several isolates of *O. formigenes* have provided the basis for dividing this genus into two major subgroupings (Jensen et al., 1994). When RFLP analyses were performed on genomic DNA isolated from various *Oxalobacter formigenes* strains, probes AP15 (SEQ ID NO. 6) and AP273 (SEQ ID NO. 10) were able to distinguish group I strains from group II strains on the Southern blot hybridizations (FIG. 6). All strains of *O. formigenes* belonging to group I (to which OxB is assigned) hybridized with both probe AP15 (SEQ ID NO. 6) and probe AP273 (SEQ ID NO. 10). Due to a characteristic slow growth of strain HC-1, only faint bands appeared in this experiment. In contrast, none of the *O. formigenes* strains assigned to group II hybridized with probe AP273 (SEQ ID NO. 10) and only BA-1 hybridized with probe AP15 (SEQ ID NO. 6). These data indicate a highly conserved homology of oxc and frc within group I strains and a less conserved homology within group II strains.

Figures 7A, 7B:
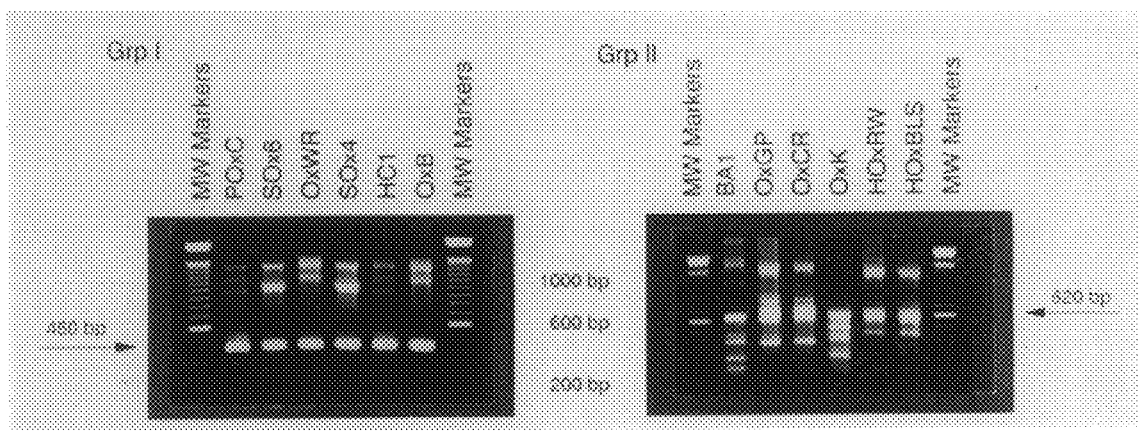
FIGS. 7A–7B show PCR-based amplification of a genetic region of the oxc gene in various strains of *O. formigenes*. Using PCR primer AP15 (SEQ ID NO. 6) and primer AP22 (SEQ ID NO. 11) as PCR primers, PCR amplification was performed using genomic DNA isolated from each of the 12 strains of *O. formigenes* listed in Table 1 as template. PCR products were size fractionated by electrophoresis through 1.2% agarose gels and observed visually using ethidium bromide (EtBr) and UV light.

To increase the sensitivity of detecting *O. formigenes*, PCR was used to amplify that portion of oxc which by RFLP appeared to differentiate the group I and group II strains. Using primer AP15 (SEQ ID NO. 6) and primer AP22 (SEQ ID NO. 11) as PCR primers to amplify a DNA segment in the carboxy-terminal region of oxc, strains assigned to group I (i.e., OxB, HC-1, OxWR, POxC, SOx-4 and SOx-6) exhibited a common band at 452 bp (FIGS. 7A–7B). In contrast, the other six strains, all belonging to group II, showed variable amplification patterns, but all showed a dominant PCR band of approximately 630 bp, with a weaker 452 bp band. Sequence analysis of this 630 bp band from strain OxK has revealed the presence of the 452 bp sequence present in the 630 bp PCR product. Close analysis of the group II strains suggest that their PCR amplification profiles are highly reproducible, suggesting group II strains may fall into three (sub)groupings: HOxBLS and HOxRW (subgroup 1), OxCR and OxGP (subgroup 2), and BA-1 and OxK (subgroup 3).

The use of PCR-based detection of the oxc gene to identify *O. formigenes* in clinical specimens was examined by comparing PCR and biochemical methods of detection. Specimen 1, known to be positive for *O. formigenes*, gave ambiguous results in biochemical testing for oxalate depletion, but exhibited the presence of the 450 bp PCR product indicative of an *O. formigenes* group I strain. Specimen 2, known to be negative for *O. formigenes*, proved negative using both PCR-based and biochemical testing. Specimen 3, known to be positive for *O. formigenes*, showed depletion of oxalate in all dilutions and revealed a PCR pattern suggestive of an *O. formigenes* group II strain. PCR amplification was not observed in the original culture or the first dilution due to the presence of inhibitors of PCR e.g., bile salts, bilirubin, etc.) which copurify with DNA.

Figures 8A, 8B:
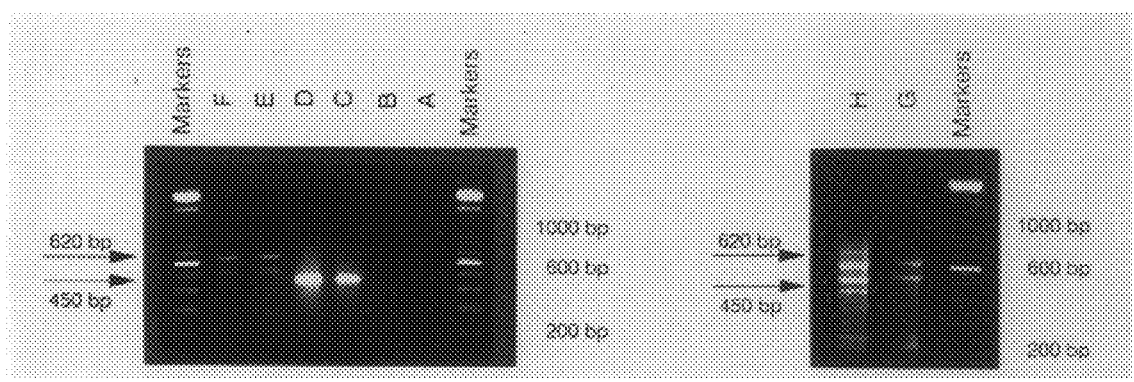
FIGS. 8A–8B show a direct analysis of fecal samples for *O. formigenes*. Oxalobacter negative stool sample (A & B) was spiked with $10^2$ (C) and $10^4$ (D) cfu of OxB or $10^3$ (E) and $10^4$ (F) cfu of OxK per 0.1 gm. DNA from an unspiked *O. formigenes*-positive stool sample diluted 1:25 (G) and 1:50 (H).

To circumvent the inhibition of the PCR by factors copurifying with the bacterial DNA, DNA isolation was performed by lysing fresh stool samples with guanidine thiocyanate followed by adsorption to and elution from glass matrices. Using this method, PCR-based detection of *O. formigenes* can be performed using fecal DNA diluted only 1:25 to 1:50 to eliminate PCR inhibitors. Sensitivity experiments using different stool samples spiked with strains OxB or OxK in the range of $10^1$ to $10^7$ cfu per 0.1 g of sample showed that as few as $10^2$ to $10^3$ cfu of *O. formigenes* per 0.1 g sample could be detected (FIGS. 8A–8B). Again, PCR-based analyses of DNA isolated directly from a stool sample known to be positive for *O. formigenes* by culture methods, showed amplification patterns indicative of a group II strain (FIGS. 8A–8B, lanes F & G).

It should be understood that the examples and embodiments described herein are for illustrative purposes only and that various modifications or changes in light thereof will be suggested to persons in the art and are to be included within the spirit and purview of this application and the scope of the appended claims.

REFERENCES

Allison, M. J., K. S. Dawson, W. R. Mayberry, J. G. Foss (1985) "*Oxalobacter formigenes* gen. nov., sp. nov.: oxalate degrading bacteria that inhabit the gastrointestinal tract," *Arch. Microbiol.* 141:1–7.

Anderson, J. T., J. G. Cornellius, A. J. Jarpe, W. E. Winter, A. B. Peck (1993) "Insulin-dependent diabetes in the NOD mouse model. II. β cell destruction in autoimmune diabetes is a $T_{H1}$ mediated event," *Autoimmunity* 15:113–122.

Baetz, A. L., M. J. Allison (1989) "Purification and Characterization of Oxalyl-Coenzyme A Decarboxylase from *Oxalobacter formigenes*," *J. Bacteriol.* 171:2605–2608.

Baetz, A. L., M. J. Allison (1990) "Purification and Characterization of Formyl-Coenzyme A Transferase from *Oxalobacter formigenes*," *J. Bacteriol.* 172:3537–3540.

Curhan, et al. (1993) "A Prospective study of dietary calcium and other nutrients and the risk of symptomatic kidney stones," *N.E.J. Med.* 328:833–838.

Costello, J., M. Hatch, E. Bourke (1976) "An enzymic method for the spectrophotometric determination of oxalic acid," *J. Lab. Clin. Med.* 87(5):903–908.

Dawson, K. A., M. J. Allison, P. A. Hartman (1980) "Isolation and some characteristics of anaerobic oxalate-degrading bacteria from ruman" *Appl. Environ. Microbiol.* 40:833–839.

Hatch, M., R. W. Freel (1996) "Oxalate transport across intestinal and renal epithelia" *Calcium Oxalate in Biological Systems*, pages 217–238, CRC Press, Boca Raton, Fla.

Hodgkinson, A. (1970) "Determination of Oxalic acid in Biological Material," *Clin. Chem.* 16(7):547–557.

Jensen, N. S., M. J. Allison (1994) "Studies on the divirsity among anaerobic oxalate-degrading bacteria now in the species *Oxalobacter formigenes*" *Abst. Ann. Mtg. Amer. Soc. Microbial.*, pages 1–29.

Lung, H., A. L. Baetz, A. B. Peck (1994) "Molecular Cloning, DNA Sequence and Gene Expression of the Oxalyl-CoA Decarboxylase Gene, oxc, from the Bacterium *Oxalobacter formigenes*," *J. Bacteriol.* 176(8):2468–2472.

Maniatis, T., E. F. Fritsch, J. Sambrook (1989) *Molecular Cloning: A Laboratory Manual*, 2d Edition, Cold Spring Harbor Laboratory, Cold Spring Harbor, N.Y.

Stacy-Phips, S., J. J. Mecca, J. B. Weiss (1995) *J. Clin. Microbiol.* 33:1054.

Yriberri, J., L. S. Posten (1980) "A semi-automatic enzymic method for estimating urinary oxalate," *Clin. Chem.* 26(7):881–884.

We claim:

1. An isolated polynucleotide molecule, comprising a nucleotide sequence that encodes a formyl-CoA transferase polypeptide derived from *Oxalobacter formigenes*.

2. The polynucleotide molecule, according to claim 1, wherein said nucleotide sequence encodes a polypeptide comprising the amino acid sequence shown in SEQ ID NO. 2.

3. The polynucleotide molecule, according to claim 1, comprising the nucleotide sequence shown in SEQ ID NO. 1.

4. The polynucleotide molecule, according to claim 1, wherein said polynucleotide molecule hybridizes under standard high-stringency conditions with a polynucleotide molecule comprising the nucleotide sequence shown in SEQ ID NO. 1.

5. A polynucleotide probe complementary with a polynucleotide sequence encoding a formyl-CoA transferase polypeptide of *Oxalobacter formigenes*, said probe comprising a nucleotide sequence shown in SEQ ID NO. 10.

6. A method for detecting *Oxalobacter formigenes* in a sample, comprising the steps of:
 (a) contacting said sample with a polynucleotide probe of claim 5 under high stringency conditions sufficient for selective hybridization of said polynucleotide probe with a DNA fragment of *Oxalobacter formigenes*; and
 (b) detecting said polynucleotide probe hybridized to said DNA fragment.

7. The method, according to claim 6, wherein said DNA fragment is immobilized on a membrane.

8. The method according to claim 6, wherein said polynucleotide probe contains a detectable label.

9. A kit for detecting the presence of *Oxalobacter formigenes* in a sample, comprising in one or more separate containers:
 (a) the polynucleotide probe of claim 5.

10. The polynucleotide molecule, according to claim 1, comprising nucleotides 162 through 1445 of SEQ ID NO. 1.

* * * * *

UNITED STATES PATENT AND TRADEMARK OFFICE
CERTIFICATE OF CORRECTION

PATENT NO. : 5,912,125

DATED : June 15, 1999

INVENTOR(S) : Ammon B. Peck, Harmeet Sidhu

It is certified that error appears in the above-identified patent and that said Letters Patent is hereby corrected as shown below:

Column 8, line 42: "GTTCT-3'" should read --GCTTCT-3'--.

Signed and Sealed this

Eleventh Day of January, 2000

Attest:

Q. TODD DICKINSON

*Attesting Officer*  *Acting Commissioner of Patents and Trademarks*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 1577 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
AAGCTTGCTT CATTTTGAGA TGTTATGCGA AGTGTTAGCA ACCCAAGTTA GTACCCTTCA      60
GCCCTTTGGG CGAAGTTTTT CTTTCTTGGC AGTTCCTTTC GGGGAAACAG CACAGAGAAT     120
AAAAACCAAA AGTTGTACCA ACGACAAGGA AATGAGAAAT TATGACTAAA CCATTAGATG     180
GAATTAATGT GCTTGACTTT ACCCACGTCC AGGCAGGTCC TGCCTGTACA CAGATGATGG     240
GTTTCTTGGG CGCAAACGTC ATCAAGATTG AAAGACGTGG TTCCGGAGAT ATGACTCGTG     300
GATGGCTGCA GGACAAACCA AATGTTGATT CCCTGTATTT CACGATGTTC AACTGTAACA     360
AACGTTCGAT TGAACTGGAC ATGAAAACCC CGGAAGGCAA AGAGCTTCTG AACAGATGA      420
TCAAGAAAGC CGACGTCATG GTCGAAAACT TCGGACCAGG CGCACTGGAC CGTATGGGCT     480
TTACTTGGGA ATACATTCAG GAACTGAATC CACGCGTCAT TCTGGCTTCC GTTAAAGGCT     540
ATGCAGAAGG CCACGCCAAC GAACACCTGA AAGTTTATGA AAACGTTGCA CAGTGTTCCG     600
GCGGTGCTGC AGCTACCACC GGTTTCTGGG ATGGTCCTCC AACCGTTTCC GGCGCTGCTC     660
TGGGTGACTC CAACTCCGGT ATGCACCTGA TGATCGGTAT TCTGGCCGCT CTGGAAATGC     720
GTCACAAAAC CGGCCGTGGT CAGAAAGTTG CCGTCGCTAT GCAGGACGCT GTTCTGAATC     780
TGGTTCGTAT CAAACTGCGT GACCAGCAAC GTCTGGAAAG AACCGGCATT CTGGCTGAAT     840
ACCCACAGGC TCAGCCTAAC TTTGCCTTCG ACAGAGACGG TAACCCACTG TCCTTCGACA     900
ACATCACTTC CGTTCCACGT GGTGGTAACG CAGGTGGCGG CGGCCAGCCA GGCTGGATGC     960
TGAAATGTAA AGGTTGGGAA ACCGATGCGG ACTCCTACGT TTACTTCACC ATCGCTGCAA    1020
ACATGTGGCC ACAGATCTGC GACATGATCG ACAAGCCAGA ATGGAAAGAC GACCCAGCCT    1080
ACAACACATT CGAAGGTCGT GTTGACAAGC TGATGGACAT CTTCTCCTTC ATCGAAACCA    1140
AGTTCGCTGA CAAGGACAAA TTCGAAGTTA CCGAATGGGC TGCCCAGTAC GGCATTCCTT    1200
GCGGTCCGGT CATGTCCATG AAAGAACTGG CTCACGATCC TTCCCTGCAG AAAGTTGGTA    1260
CCGTCGTTGA AGTTGTCGAC GAAATTCGTG GTAACCACCT GACCGTTGGC GCACCGTTCA    1320
AATTCTCCGG ATTCCAGCCG GAAATTACCC GTGCTCCGCT GTTGGGCGAA CATACCGACG    1380
AAGTTCTGAA AGAACTGGGT CTTGACGATG CCAAGATCAA GGAACTGCAT GCAAAACAGG    1440
TAGTTTGATC CGTCAGACTT TCTGGGCAAA ACGGCACTCT CCGGAGTGCC GTTTTTTGTC    1500
ACACGAAACC TAATCAAACA AGCACGTGCA ATGATTCCAC ATCATTGCGG CCACATTCAT    1560
CCTTCGGGTC ATTACTG                                                    1577
```

(2) INFORMATION FOR SEQ ID NO:2:

(i) SEQUENCE CHARACTERISTICS:
       (A) LENGTH: 428 amino acids
       (B) TYPE: amino acid (C) STRANDEDNESS: single
(D) TOPOLOGY: linear (ii) MOLECULE TYPE: protein (xi) SEQUENCE DESCRIPTION: SEQ ID NO:2:

```
Met Thr Lys Pro Leu Asp Gly Ile Asn Val Leu Asp Phe Thr His Val
 1               5                  10                  15

Gln Ala Gly Pro Ala Cys Thr Gln Met Met Gly Phe Leu Gly Ala Asn
                20                  25                  30

Val Ile Lys Ile Glu Arg Arg Gly Ser Gly Asp Met Thr Arg Gly Trp
            35                  40                  45

Leu Gln Asp Lys Pro Asn Val Asp Ser Leu Tyr Phe Thr Met Phe Asn
        50                  55                  60

Cys Asn Lys Arg Ser Ile Glu Leu Asp Met Lys Thr Pro Glu Gly Lys
65                  70                  75                  80

Glu Leu Leu Glu Gln Met Ile Lys Lys Ala Asp Val Met Val Glu Asn
                85                  90                  95

Phe Gly Pro Gly Ala Leu Asp Arg Met Gly Phe Thr Trp Glu Tyr Ile
                100                 105                 110

Gln Glu Leu Asn Pro Arg Val Ile Leu Ala Ser Val Lys Gly Tyr Ala
            115                 120                 125

Glu Gly His Ala Asn Glu His Leu Lys Val Tyr Glu Asn Val Ala Gln
        130                 135                 140

Cys Ser Gly Gly Ala Ala Ala Thr Thr Gly Phe Trp Asp Gly Pro Pro
145                 150                 155                 160

Thr Val Ser Gly Ala Ala Leu Gly Asp Ser Asn Ser Gly Met His Leu
                165                 170                 175

Met Ile Gly Ile Leu Ala Ala Leu Glu Met Arg His Lys Thr Gly Arg
                180                 185                 190

Gly Gln Lys Val Ala Val Ala Met Gln Asp Ala Val Leu Asn Leu Val
            195                 200                 205

Arg Ile Lys Leu Arg Asp Gln Gln Arg Leu Glu Arg Thr Gly Ile Leu
        210                 215                 220

Ala Glu Tyr Pro Gln Ala Gln Pro Asn Phe Ala Phe Asp Arg Asp Gly
225                 230                 235                 240

Asn Pro Leu Ser Phe Asp Asn Ile Thr Ser Val Pro Arg Gly Gly Asn
                245                 250                 255

Ala Gly Gly Gly Gln Pro Gly Trp Met Leu Lys Cys Lys Gly Trp
                260                 265                 270

Glu Thr Asp Ala Asp Ser Tyr Val Tyr Phe Thr Ile Ala Ala Asn Met
        275                 280                 285

Trp Pro Gln Ile Cys Asp Met Ile Asp Lys Pro Glu Trp Lys Asp Asp
        290                 295                 300

Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
                325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
        355                 360                 365

Val Glu Val Val Asp Glu Ile Arg Gly Asn His Leu Thr Val Gly Ala
        370                 375                 380

Pro Phe Lys Phe Ser Gly Phe Gln Pro Glu Ile Thr Arg Ala Pro Leu
```

| | | | |
|---|---|---|---|
| 385 | 390 | 395 | 400 |

Leu Gly Glu His Thr Asp Glu Val Leu Lys Glu Leu Gly Leu Asp Asp
             405                   410                   415

Ala Lys Ile Lys Glu Leu His Ala Lys Gln Val Val
            420                   425

(2) INFORMATION FOR SEQ ID NO:3:

(i) SEQUENCE CHARACTERISTICS:
        (A) LENGTH: 2088 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ATTTGTTTAA ATTGACCTGA ATCAATATTG CCGGATTGAT CTAGGTCAAT GAATGCAAA       60
TGACTTATGT CAATGGTGCC AAATTGACCT AGGTCAACGG GATTTTTAAA GGGTATGCGG     120
CATACTCGGA ATTGACGTTA AACAACGTTT ATCAAAACCA ACCAAAGAAA GGTATTACTC     180
ATGAGTAACG ACGACAATGT AGAGTTGACT GATGGCTTTC ATGTTTTGAT CGATGCCCTG     240
AAAATGAATG ACATCGATAC CATGTATGGT GTTGTCGGCA TTCCTATCAC GAACCTGGCT     300
CGTATGTGGC AAGATGACGG TCAGCGTTTT TACAGCTTCC GTCACGAACA ACACGCAGGT     360
TATGCAGCTT CTATCGCCGG TTACATCGAA GGAAAACCTG GCGTTTGCTT GACCGTTTCC     420
GCCCCTGGCT TCCTGAACGG CGTGACTTCC CTGGCTCATG CAACCACCAA CTGCTTCCCA     480
ATGATCCTGT TGAGCGGTTC CAGTGAACGT GAAATCGTCG ATTTCCAAGA CGGCGATTAC     540
GAAGAAATGG ATCAGATGAA TGTTGCACGT CCACACTGCA AAGCTTCTTT CCGTATCAAC     600
AGCATCAAAG ACATTCCAAT CGGTATCGCT CGTGCAGTTC GCACCGCTGT ATCCGGACGT     660
CCAGGTGGTG TTTACGTTGA CTTCCCAGCA AAACTGTTCG GTCAGACCAT TTCTGTAGAA     720
GAAGCTAACA AACTGCTCTT CAAACCAATC GATCCAGCTC CGGCACAGAT TCTTGCTGAA     780
GACGCTATCG CTCGCGCTGC TGACCTGATC AAGAACGCCA ACGTCCAGT ATCATGCTG      840
GGTAAAGGCG CTGCATACGC ACAATGCGAC GACGAAATCC GCGCACTGGT TGAAGAAACC     900
GGCATCCCAT TCCTGCCAAT GGGTATGGCT AAAGGCCTGC TGCCTGACAA CCATCCACAA     960
TCCGCTGCTG CAACCCGTGC TTTCGCACTG GCACAGTGTG ACGTTTGCGT ACTGATCGGC    1020
GCTCGTCTGA ACTGGCTGAT GCAGCACGGT AAAGGCAAAA CCTGGGGCGA CGAACTGAAG    1080
AAATACGTTC AGATCGACAT CCAGGCTAAC GAAATGGACA GCAACCAGCC TATCGCTGCA    1140
CCAGTTGTTG GTGACATCAA GTCCGCCGTT TCCCTGCTCC GCAAAGCACT GAAAGGCGCT    1200
CCAAAAGCTG ACGCTGAATG GACCGGCGCT CTGAAAGCCA AGTTGACGG CAACAAAGCC    1260
AAACTGGCTG GCAAGATGAC TGCCGAAACC CCATCCGGAA TGATGAACTA CTCCAATTCC    1320
CTGGGCGTTG TTCGTGACTT CATGCTGGCA AATCCGGATA TTTCCCTGGT TAACGAAGGC    1380
GCTAATGCAC TCGACAACAC TCGTATGATT GTTGACATGC TGAAACCACG CAAACGTCTT    1440
GACTCCGGTA CCTGGGGTGT TATGGGTATT GGTATGGGCT ACTGCGTTGC TGCAGCTGCT    1500
GTTACCGGCA AACCGGTTAT CGCTGTTGAA GGCGATAGCG CATTCGGTTT CTCCGGTATG    1560
GAACTGGAAA CCATCTGCCG TTACAACCTG CCAGTTACCG TTATCATCAT GAACAATGGT    1620
GGTATCTATA AAGGTAACGA AGCAGATCCA CAACCAGGCG TTATCTCCTG TACCCGTCTG    1680
ACCCGTGGTC GTTACGACAT GATGATGGAA GCATTTGGCG GTAAAGGTTA TGTTGCCAAT    1740
ACTCCAGCAG AACTGAAAGC TGCTCTGGAA GAAGCTGTTG CTTCCGGCAA ACCATGCCTG    1800
```

```
ATCAACGCGA TGATCGATCC AGACGCTGGT GTCGAATCTG GCCGTATCAA GAGCCTGAAC    1860

GTTGTAAGTA AAGTTGGCAA GAAATAATTA GCCCAACTTT GATGACCGGT TACGACCGGT    1920

CACATAAAGT GTTCGAATGC CCTTCAAGTT TACTTGAAGG GCATTTTTTT ACCTTGCAGT    1980

TTATAAACAG GAAAAATTGT ATTCAGAGCG GAAAAGCAGA TTTAAGCCAC GAGAAACATT    2040

CTTTTTTATT GAAAATTGCC ATAAACACAT TTTTAAAGCT GGCTTTTT                  2088
```

(2) INFORMATION FOR SEQ ID NO:4:

(i) SEQUENCE CHARACTERISTICS:
        (A) LENGTH: 568 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Ser Asn Asp Asp Asn Val Glu Leu Thr Asp Gly Phe His Val Leu
 1               5                  10                  15

Ile Asp Ala Leu Lys Met Asn Asp Ile Asp Thr Met Tyr Gly Val Val
            20                  25                  30

Gly Ile Pro Ile Thr Asn Leu Ala Arg Met Trp Gln Asp Asp Gly Gln
        35                  40                  45

Arg Phe Tyr Ser Phe Arg His Glu Gln His Ala Gly Tyr Ala Ala Ser
    50                  55                  60

Ile Ala Gly Tyr Ile Glu Gly Lys Pro Gly Val Cys Leu Thr Val Ser
65                  70                  75                  80

Ala Pro Gly Phe Leu Asn Gly Val Thr Ser Leu Ala His Ala Thr Thr
                85                  90                  95

Asn Cys Phe Pro Met Ile Leu Leu Ser Gly Ser Ser Glu Arg Glu Ile
            100                 105                 110

Val Asp Leu Gln Gln Gly Asp Tyr Glu Glu Met Asp Gln Met Asn Val
        115                 120                 125

Ala Arg Pro His Cys Lys Ala Ser Phe Arg Ile Asn Ser Ile Lys Asp
    130                 135                 140

Ile Pro Ile Gly Ile Ala Arg Ala Val Arg Thr Ala Val Ser Gly Arg
145                 150                 155                 160

Pro Gly Gly Val Tyr Val Asp Leu Pro Ala Lys Leu Phe Gly Gln Thr
                165                 170                 175

Ile Ser Val Glu Glu Ala Asn Lys Leu Leu Phe Lys Pro Ile Asp Pro
            180                 185                 190

Ala Pro Ala Gln Ile Pro Ala Glu Asp Ala Ile Ala Arg Ala Ala Asp
        195                 200                 205

Leu Ile Lys Asn Ala Lys Arg Pro Val Ile Met Leu Gly Lys Gly Ala
    210                 215                 220

Ala Tyr Ala Gln Cys Asp Asp Glu Ile Arg Ala Leu Val Glu Glu Thr
225                 230                 235                 240

Gly Ile Pro Phe Leu Pro Met Gly Met Ala Lys Gly Leu Leu Pro Asp
                245                 250                 255

Asn His Pro Gln Ser Ala Ala Ala Thr Arg Ala Phe Ala Leu Ala Gln
            260                 265                 270

Cys Asp Val Cys Val Leu Ile Gly Ala Arg Leu Asn Trp Leu Met Gln
        275                 280                 285

His Gly Lys Gly Lys Thr Trp Gly Asp Glu Leu Lys Lys Tyr Val Gln
    290                 295                 300
```

```
Ile Asp Ile Gln Ala Asn Glu Met Asp Ser Asn Gln Pro Ile Ala Ala
305                 310                 315                 320

Pro Val Val Gly Asp Ile Lys Ser Ala Val Ser Leu Leu Arg Lys Ala
            325                 330                 335

Leu Lys Gly Ala Pro Lys Ala Asp Ala Glu Trp Thr Gly Ala Leu Lys
            340                 345                 350

Ala Lys Val Asp Gly Asn Lys Ala Lys Leu Ala Gly Lys Met Thr Ala
        355                 360                 365

Glu Thr Pro Ser Gly Met Met Asn Tyr Ser Asn Ser Leu Gly Val Val
        370                 375                 380

Arg Asp Phe Met Leu Ala Asn Pro Asp Ile Ser Leu Val Asn Glu Gly
385                 390                 395                 400

Ala Asn Ala Leu Asp Asn Thr Arg Met Ile Val Asp Met Leu Lys Pro
                405                 410                 415

Arg Lys Arg Leu Asp Ser Gly Thr Trp Gly Val Met Gly Ile Gly Met
                420                 425                 430

Gly Tyr Cys Val Ala Ala Ala Val Thr Gly Lys Pro Val Ile Ala
        435                 440                 445

Val Glu Gly Asp Ser Ala Phe Gly Phe Ser Gly Met Glu Leu Glu Thr
450                 455                 460

Ile Cys Arg Tyr Asn Leu Pro Val Thr Val Ile Ile Met Asn Asn Gly
465                 470                 475                 480

Gly Ile Tyr Lys Gly Asn Glu Ala Asp Pro Gln Pro Gly Val Ile Ser
            485                 490                 495

Cys Thr Arg Leu Thr Arg Gly Arg Tyr Asp Met Met Glu Ala Phe
            500                 505                 510

Gly Gly Lys Gly Tyr Val Ala Asn Thr Pro Ala Glu Leu Lys Ala Ala
            515                 520                 525

Leu Glu Glu Ala Val Ala Ser Gly Lys Pro Cys Leu Ile Asn Ala Met
530                 535                 540

Ile Asp Pro Asp Ala Gly Val Gly Ser Gly Arg Ile Lys Ser Leu Asn
545                 550                 555                 560

Val Val Ser Lys Val Gly Lys Lys
                565
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GAGCGATACC GATTGGA                                                    17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GCACAATGCG ACGACGA                                                    17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CAGGTTATGC AGCTTCT                                                    17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGATGGTTGT CAGGCAG                                                    17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATACTCGGAA TTGACGT                                                    17

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TTCATGTCCA GTTCAATCGA ACG                                             23

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GTAGTTCATC ATTCCGG                                                    17
```